United States Patent
Kim

(10) Patent No.: US 10,695,314 B2
(45) Date of Patent: Jun. 30, 2020

(54) ANTIMICROBIAL COMPOSITION CONTAINING 7,10-EPOXYOCTADECA-7,9-DIENOIC ACID AS ACTIVE INGREDIENT

(71) Applicant: KYUNGPOOK NATIONAL UNIVERSITY INDUSTRY-ACADEMIC COOPERATION FOUNDATION, Daegu (KR)

(72) Inventor: Hak Ryul Kim, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 0 days.

(21) Appl. No.: 16/096,375

(22) PCT Filed: Apr. 25, 2017

(86) PCT No.: PCT/KR2017/004359
§ 371 (c)(1),
(2) Date: Oct. 25, 2018

(87) PCT Pub. No.: WO2017/188692
PCT Pub. Date: Nov. 2, 2017

(65) Prior Publication Data
US 2019/0133989 A1 May 9, 2019

(30) Foreign Application Priority Data

Apr. 25, 2016 (KR) .................. 10-2016-0049916
Nov. 1, 2016 (KR) .................. 10-2016-0144516

(51) Int. Cl.
| | |
|---|---|
| *A61K 31/341* | (2006.01) |
| *A61K 31/43* | (2006.01) |
| *A23L 33/10* | (2016.01) |
| *A23K 20/121* | (2016.01) |
| *A61Q 17/00* | (2006.01) |
| *A23K 20/174* | (2016.01) |
| *A23K 10/18* | (2016.01) |

(Continued)

(52) U.S. Cl.
CPC ............ *A61K 31/341* (2013.01); *A01N 43/08* (2013.01); *A23K 10/18* (2016.05); *A23K 20/121* (2016.05); *A23K 20/142* (2016.05); *A23K 20/158* (2016.05); *A23K 20/174* (2016.05); *A23K 20/195* (2016.05); *A23K 20/20* (2016.05); *A23K 20/24* (2016.05); *A23K 50/10* (2016.05); *A23L 2/52* (2013.01); *A23L 33/10* (2016.08); *A23L 33/127* (2016.08); *A23L 33/155* (2016.08); *A23L 33/16* (2016.08); *A61K 8/4973* (2013.01); *A61K 31/43* (2013.01); *A61K 45/06* (2013.01); *A61P 31/04* (2018.01); *A61Q 17/005* (2013.01); *A23V 2002/00* (2013.01); *Y02A 50/473* (2018.01); *Y02A 50/481* (2018.01)

(58) Field of Classification Search
CPC .. A61K 2300/00; A61K 31/341; A61K 31/43; A61K 45/06; A61K 8/49; A23V 2002/00; A23V 2002/30; A23V 2250/02; A23V 2250/156; A23V 2250/1578; A23V 2250/16; A23V 2250/161; A23V 2250/186; A23V 2250/70; A23V 2250/704; A01K 2217/072; A01K 2217/15; A01K 2217/203; A01K 2217/206; A01K 2217/30; A01K 2227/105; A01K 2267/03; A01K 2267/0362; A01K 2267/0275; A01N 43/08; A23K 10/18; A23K 20/121; A23K 20/142; A23K 20/158; A23K 20/174; A23K 20/195; A23K 20/20; A23K 20/24; A23K 50/10; A23L 2/52; A23L 33/10; A23L 33/127; A23L 33/155; A23L 33/16; A61P 31/04; A61Q 17/00; C07K 2319/70; C12N 15/8509; C12N 2800/30; C12N 2840/002; C12N 9/6475; C12N 9/90; Y02A 50/473; Y02A 50/481
See application file for complete search history.

(56) References Cited

U.S. PATENT DOCUMENTS

| | | |
|---|---|---|
| 8,426,620 B2 | 4/2013 | Kim et al. |
| 9,012,505 B2 | 4/2015 | Zhang et al. |

(Continued)

FOREIGN PATENT DOCUMENTS

| | | |
|---|---|---|
| JP | 2012 516889 A | 7/2012 |
| JP | 2014 513670 A | 6/2014 |

(Continued)

OTHER PUBLICATIONS

FDA Consumer Health Information, 2013 (Year: 2013).*

(Continued)

*Primary Examiner* — Umamaheswari Ramachandran
(74) *Attorney, Agent, or Firm* — Norris McLaughlin, P.A.

(57) ABSTRACT

The present invention relates to an antimicrobial composition comprising, as an active ingredient, 7,10-epoxyoctadeca-7,9-dienoic acid or a combination of 7,10-epoxyoctadeca-7,9-dienoic acid and another antibiotic. The growth of bacteria can be effectively inhibited regardless of the class of antibiotics when using the antimicrobial composition of the present invention. Therefore, the antimicrobial composition of the present invention can be useful in related pharmaceutical, food and cosmetic industries requiring the inhibition of bacterial growth.

5 Claims, 10 Drawing Sheets

(51) Int. Cl.

| | |
|---|---|
| A23K 20/142 | (2016.01) |
| A61K 45/06 | (2006.01) |
| A23K 50/10 | (2016.01) |
| A61K 8/49 | (2006.01) |
| A23K 20/20 | (2016.01) |
| A23K 20/24 | (2016.01) |
| A01N 43/08 | (2006.01) |
| A23K 20/158 | (2016.01) |
| A23K 20/195 | (2016.01) |
| A23L 33/16 | (2016.01) |
| A23L 33/155 | (2016.01) |
| A61P 31/04 | (2006.01) |
| A23L 2/52 | (2006.01) |

(56) References Cited

U.S. PATENT DOCUMENTS

| | | |
|---|---|---|
| 9,464,032 B2 | 10/2016 | Bolla et al. |
| 2010/0197621 A1 | 8/2010 | Henry et al. |
| 2012/0245107 A1 | 9/2012 | Henry et al. |
| 2012/0302774 A1 | 11/2012 | Kim et al. |
| 2014/0128335 A1 | 5/2014 | Bolla et al. |
| 2017/0015617 A1 | 1/2017 | Bolla et al. |

FOREIGN PATENT DOCUMENTS

| | | |
|---|---|---|
| KR | 10 2012 0131529 A | 12/2012 |
| WO | 2008 150477 A2 | 12/2008 |

OTHER PUBLICATIONS

Bush, Merck Manuals, 2018 (Year: 2018).*
Werth, Merck Manual, 2018 (Year: 2018).*
Bacterial Infections 101, 2016 (Year: 2016).*
Mayo Clinic, Food Poisoning, 2016 (Year: 2016).*
Sanchez, Current Hepatology Reports (2019) 18:28-35 (Year: 2019).*
Rteta, Advances in Preventive Medicine, 2019 (Year: 2019).*
CDC (https://www.cdc.gov/media/releases/2016/p0303-superbugs.html, 2016) (Year: 2016).*
CDC, 2019, https://www.cdc.gov/drugresistance/biggest-threats.html (Year: 2019).*
English version of the International Search Report completed Jul. 10, 2017 for corresponding PCT/KR2017/004359.
Mostafa, A.A., et al., "Antimicrobial activity of some plant extracts against bacterial strains causing food poisoning diseases"; Saudi Journal of Biological Sciences 25 (2018) pp. 361-366.
Tiina, M., et al., "Antibacterial effect of the glucose oxidase-glucose system on food-poisoning organisms"; International Journal of Food Microgiology: 8 (1989) pp. 165-174.
Behbahani, B.A., et al., "Antibacterial activities, phytochemical analysis and chemical composition Makhlaseh extracts against the growth of . . . "; Microbial Pathogenesis 114 (2018) pp. 204-208.

* cited by examiner

A : Vancomycin (100μg)
B : Oxacillin (100μg)
C : Ampicillin (100μg)
D : Streptomycin (100μg)
E : Penicillin (100μg)
F : EODA (100μg)

A: Vancomycin (100μg)
B: Oxacillin (100μg)
C: EODA(50μg)
D: EODA(100μg)
E: EODA(200μg)
F: EODA(400μg)

A : EODA (100μg)
B : Vancomycin (100μg)
C : Oxacillin (100μg)

100 # ANTIMICROBIAL COMPOSITION CONTAINING 7,10-EPOXYOCTADECA-7,9-DIENOIC ACID AS ACTIVE INGREDIENT

This application is a 371 of PCT/KR2017/004359, filed Apr. 25, 2017, which claims foreign priority benefit under 35 U.S.C. § 119 of the Korean Patent Application No. 10-2016-0049916, filed Apr. 25, 2016 and Korean Patent Application No. 10-2016-0144516, filed Nov. 1, 2016, the disclosures of which are incorporated herein by reference.

TECHNICAL FIELD

The present invention relates to an antimicrobial composition comprising 7,10-epoxyoctadeca-7,9-dienoic acid as an active ingredient.

BACKGROUND ART

Furan fatty acids (F-acids) are a large group of fatty acids characterized by a furan ring, which carry at one α-position an unbranched fatty acid chain with 9, 11, or 13 carbon atoms and at the other α-position a short straight-chain alkyl group with 3 or 5 carbon atoms. Mostly two β-positions of the furan ring are substituted by either one or two methyl residues or another group. F-acids without any substitutions on both β-positions of the furan ring were also found in the seed oil of Exocarpus cupressiformis. F-acids are widely distributed in nature as trace components of plants, fishes, amphibians, reptiles, microorganisms and mammals including human.

Although the biological role of F-acids in the biological system is not fully understood, it has been pointed out that F-acids can be involved in various important biological functions acting as antioxidant, antitumoral and antithrombotic. In some fishes, F-acids include up to 25% of the acids in the liver lipids and accumulate during the spawning season, indicating a possible correlation between F-acids and the fertilization process. The correlation between consumption of fish rich in F-acid and protection against coronary heart disease mortality has been confirmed in several studies [(Spiteller, 2005, Lipids 40(8): 755-771), (Ishii et al., 1989, Chem Pharm Bull 37(5):1396-1398), (Graff et al., 1984, Biochim Biophys Acta 799(2):143-150), (Parker et al., 1977, J Med Chem 20(6):781-791)]. F-acid has also been reported to have inhibitory effects on blood platelets aggregation and to have potential antitumor activity. F-acids were found to prevent oxidation of linoleic acid and act as antioxidants in plants. Some studies demonstrated that F-acids underwent oxidation by ring opening to form dioxoenes in the presence of linoleic acid as co-substrate, demonstrating that F-acid acted as a radical scavenger.

Biosynthesis of F-acids is complicated and different. The biogenetic precursor of the most F-acids is known to be linoleic acid. It was recognized that plants synthesized the basic skeleton of F-acids. However, study with the radio-labeled feeding to fish indicated that fish synthesized neither the alkyl side chain nor the furan ring of F-acids. Therefore, F-acids in fish were considered to be originated from diet, especially algae. Consequently, F-acids are introduced into the human body through the diet like vegetables and fish. Diet-derived F-acids are incorporated into the tissue and blood of mammals, especially into phospholipids where they might act as radical scavengers resulting into inhibition of blood platelet aggregation.

As described above, various physiological activities of F-acids are well known. However, antimicrobial activity and antimicrobial effect against antibiotic combination treatment have not yet been confirmed.

DISCLOSURE

Technical Problem

It is an object of the present invention to provide an antimicrobial composition comprising, as an active ingredient, 7,10-epoxyoctadeca-7,9-dienoic acid alone, or a combination of 7,10-epoxyoctadeca-7,9-dienoic acid and another antibiotic.

Another object of the present invention is to provide a pharmaceutical composition, a cosmetic composition, a food composition, an animal feed composition, a disinfectant, or an antimicrobial adjuvant for killing antibiotic resistant bacteria for the prevention or treatment of a bacterial infectious disease comprising the antimicrobial composition.

Technical Solution

In order to solve the above-mentioned problems, the present invention provides an antimicrobial composition comprising, as an active ingredient, 7,10-epoxyoctadeca-7,9-dienoic acid alone, or a combination of 7,10-epoxyoctadeca-7,9-dienoic acid and another antibiotic.

The present invention also provides a pharmaceutical composition for the prevention or treatment of a bacterial infectious disease comprising the antimicrobial composition.

In addition, the present invention provides a cosmetic composition comprising the antimicrobial composition.

The present invention also provides a food composition comprising the antimicrobial composition.

The present invention also provides an animal feed composition comprising the antimicrobial composition.

The present invention also provides a disinfectant comprising the antimicrobial composition.

Also, provided is an antimicrobial adjuvant for killing antibiotic resistant bacteria comprising the antimicrobial composition.

Advantageous Effects

The antimicrobial composition comprising 7,10-epoxyoctadeca-7,9-dienoic acid alone as an active ingredient of the present invention, or a combination of 7,10-epoxyoctadeca-7,9-dienoic acid and another antibiotic is excellent in antimicrobial activity and is excellent in prevention, improvement, or therapeutic effect against bacterial infectious diseases, and thus is suitable for use as a pharmaceutical, cosmetic, food, animal feed composition, a disinfectant, and an antimicrobial adjuvant for killing antibiotic resistant bacteria.

In addition, when an antimicrobial composition comprising a combination of 7,10-epoxyoctadeca-7,9-dienoic acid and another antibiotic is used, a synergistic effect on the antimicrobial activity is exhibited regardless of the class of antibiotics, and thus can effectively inhibit the growth of bacteria. Therefore, it can be usefully used in related pharmaceutical, food, animal feed additive, and cosmetic industries requiring the inhibition of bacterial growth.

MODES OF THE INVENTION

Figure 1:
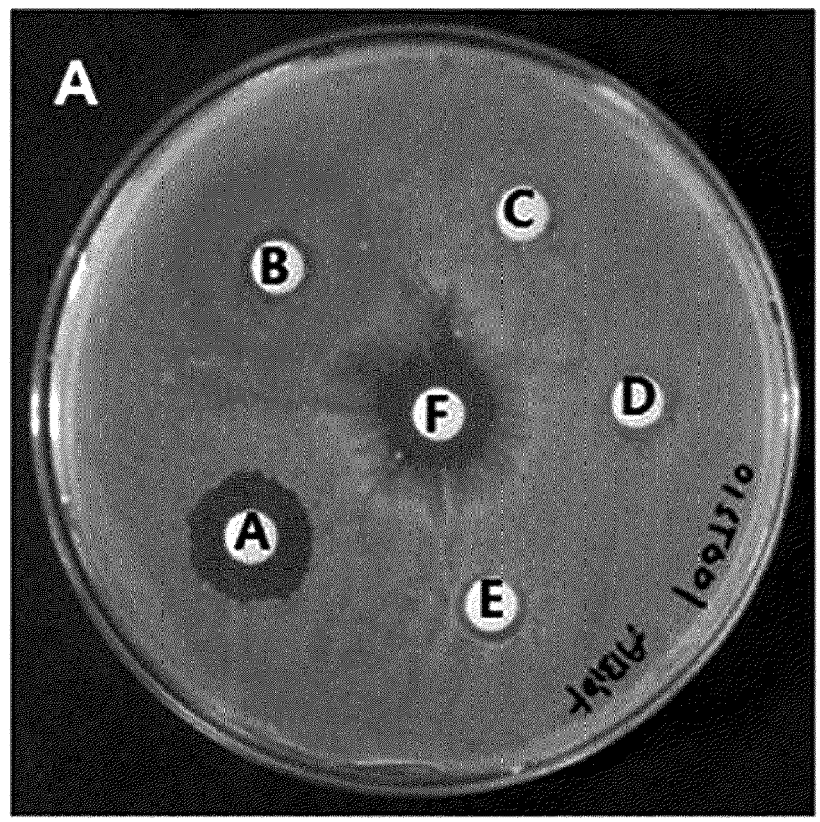
FIG. 1 is a diagram illustrating the results of confirming the antimicrobial activity of various antimicrobial agents and 7,10-epoxyoctadeca-7,9-dienoic acid (7,10-EODA) on multidrug-resistant *Staphylococcus* (MDRSA 01ST001) using a solid medium according to one embodiment of the present invention.

The present invention provides an antimicrobial composition comprising, as an active ingredient, 7,10-epoxyoctadeca-7,9-dienoic acid alone, or a combination of 7,10-epoxyoctadeca-7,9-dienoic acid and another antibiotic.

In the present invention, the "7,10-epoxyoctadeca-7,9-dienoic acid" is a compound represented by [Formula 1] below:

[Formula 1]

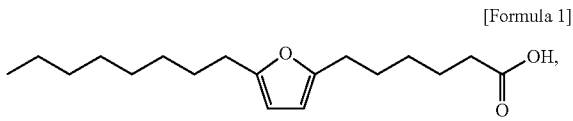 [SMILES: CCCCCCCCc1ccc(CCCCCC(=O)O)o1]

in which on a $C_{18}$ fatty acid chain, carbons 7 and 10 are linked by an epoxy structure, and a furan ring composed of carbons 7, 8, 9, and 10 is formed.

The 7,10-epoxyoctadeca-7,9-dienoic acid (7,10-EODA) may be chemically synthesized or obtained from nature.

For example, the 7,10-epoxyoctadeca-7,9-dienoic acid (EODA) may be prepared by adding hexane to 7,10-dihydroxy-8(E)-octadecenoic acid (DOD) followed by mixture and then heat treatment.

The 7,10-dihydroxy-8(E)-octadecenoic acid (DOD) is a type of a hydroxy fatty acid, and has a structure having a total of two hydroxyl groups on a $C_{18}$ fatty acid chain, each at carbon 8 and 10, and having a trans double bond between carbon 8 and 9.

The mixing ratio of 7,10-dihydroxy-8(E)-octadecenoic acid (DOD) and hexane may be determined appropriately. However, for efficient mixing with 7,10-dihydroxy-8(E)-octadecenoic acid (DOD) and production reaction, hexane may preferably be mixed in an amount corresponding to 0.5 to 1,000 times that of the used 7,10-dihydroxy-8(E)-octadecenoic acid (DOD), and more preferably, 10 to 1000 µl of hexane per 10 mg of 7,10-dihydroxy-8(E)-octadecenoic acid (DOD) may be mixed.

The heat treatment after the mixing of the 7,10-dihydroxy-8(E)-octadecenoic acid (DOD) and hexane may preferably be performed at 30 to 150° C. for 1 to 150 hours, and more preferably, at 90 to 95° C. for 12 to 96 hours.

When the antimicrobial composition of the present invention includes 7,10-epoxyoctadeca-7,9-dienoic acid alone, the 7,10-epoxyoctadeca-7,9-dienoic acid may be present at a concentration of 0.01 to 3,000 µg/ml. If the concentration is 0.01 µl/ml or less, the antimicrobial activity may not be exhibited. If the concentration exceeds 3,000 µg/ml, it may be toxic to the human body.

When the antimicrobial composition of the present invention includes a combination of 7,10-epoxyoctadeca-7,9-dienoic acid and another antibiotic as an active ingredient, the other antibiotic may be a beta-lactam or non-beta-lactam antibiotics, but are not limited thereto.

Beta-lactam antibiotics inhibit bacterial cell wall synthesis and exhibit antibacterial activity. The non-beta-lactam antibiotic refers to an antibiotic that inhibits protein synthesis, inhibits DNA/RNA synthesis, and exhibits an antimicrobial activity by cell membrane destruction.

The beta-lactam antibiotics may be at least one kind selected from the group consisting of penicillin class, Cephalosporin class, Carbapenem class, Monobactam class, and vancomycin class that are well known in the field of the present invention, but are not limited thereto.

The penicillin antibiotics may be at least one kind selected from the group consisting of Benzylpenicillin, Penoxymethylpenicillin, Ampicillin, Amoxycillin, Bacampicillin, Methicillin, Oxacillin, Cloxacillin, Piperacillin, Carbenicillin, and Ticarcillin, but are not limited thereto.

The Cephalosporin antibiotics may be at least one kind selected from the group consisting of Cephradine, Cefadroxil, Cephalexin, Cefazolin, Cephapirin, Cefaclor, Cefuroxime, Cefamandole, Cefotiam, Cefoxitin, Cefixime, Cefpodoxime, Cefotaxime, and Ceftriaxone, but are not limited thereto.

The Carbapenem antibiotics may be at least one kind selected from the group consisting of Tienam, Meropenem, imipenem, Doripenem, and Ertapenem, but are not limited thereto.

The vancomycin antibiotics may be vancomycin or teicoplanin, but are not limited thereto.

The non-beta-lactam antibiotics may be at least one kind selected from the group consisting of aminoglycoside class, Tetracycline class, Macrolide class, quinolone class, rifampicin class, Sulfonamides class, Polypeptide class, Lincosamide class, a fluoroquinolone class, and Cephalosporin class, but are not limited thereto.

The aminoglycoside antibiotics may be at least one kind selected from the group consisting of Amikacin, Sisomycin, arbekacin, Gentamycin, Kanamycin, Neomycin, Spectinomycin, netilmicin, paromomycin, Streptomycin, and tobramycin, but are not limited thereto.

The Tetracycline antibiotics may be at least one kind selected from the group consisting of Chlortetracycline, Oxytetracycline, Tetracycline, Minocycline, and Doxycycline, but are not limited thereto.

The Macrolide antibiotics may be at least one kind selected from the group consisting of Erythromycin, Spiramycin, and Tylosin, but are not limited thereto.

The quinolone antibiotics may be at least one kind selected from the group consisting of nalidixic acid, Moxifloxacin, Ofloxacin, trovan, and levofloxacin, but are not limited thereto.

The rifampicin antibiotics may be rifamycin, rifampicin, or Rifaximin, but are not limited thereto.

The Sulfonamides antibiotics may be at least one kind selected from sulfamethazine, sulfadimidine, sulfachlorpyrazine, Sulfaclozine, sulfadimethoxine, sulfachlorpyridazine, sulfadiazine, sulfamerazine, sulfamethoxazole, sulfaguanidine, sulfadoxine, and sulfathiazole, but are not limited thereto.

The polypeptide antibiotics may be Polymyxin B or Bacitracin, but are not limited thereto.

The Lincosamide antibiotics may be Lincomycin or Clindamycin, but are not limited thereto.

The fluoroquinolone antibiotics may be at least one kind selected from the group consisting of Norfloxacin, Ciprofloxacin, Enrofloxacin, Ofloxacin, and pefloxacin, but are not limited thereto.

The Cephalosporin antibiotics may be at least one kind selected from the group consisting of Cephalexin, Cefradine, Cefazolin, Cephaloridine, Cefaclor, Ceftezole, Cefamandole, Cefuroxime, Cefoxitin, Cefpiramide, cefoperazone, moxalactam, ceftiofur, and Cefuzonam, but are not limited thereto.

In one embodiment of the present invention, when the antimicrobial composition of the present invention includes a combination of 7,10-epoxyoctadeca-7,9-dienoic acid and another antibiotic, the 7,10-epoxyoctadeca-7,9-dienoic acid is treated together with another antibiotic and was not antagonized, and a synergistic effect on the antimicrobial activity against various resistant $Staphylococcus\ aureus$ is exhibited regardless of the class of antibiotics in combination with antibiotics. In addition, the 7,10-EODA of the present invention is excellent in antimicrobial activity and growth inhibition effect in combination with various antibiotics besides beta-lactam antibiotics, and can be usefully used in related pharmaceutical, food, and cosmetic industries.

When the antimicrobial composition of the present invention includes a combination of 7,10-epoxyoctadeca-7,9-dienoic acid and another antibiotic, the amount of 7,10-epoxyoctadeca-7,9-dienoic acid (7,10-EODA) among the antimicrobial composition may be variously selected depending on the target microorganism, and is preferably included at a concentration of 0.01 to 5,000 µg/ml. If the concentration is less than 0.01 µg/ml, the antimicrobial activity may not be exhibited. If the concentration is more than 5,000 µg/ml, it may be toxic to the human body.

The antimicrobial composition has an antibacterial effect on all kinds of bacteria. Examples of the bacteria having the antibacterial effect of the antimicrobial composition of the present invention include $Staphylococcus,\ Staphylococcus\ aureus,\ Escherichia\ coli,\ Salmonella\ enteritidis,\ Streptococcus\ pyogenes,\ Pseudomonas\ aeruginosa$, and $Clostridium\ difficile$.

In the present invention, the term "$Staphylococcus\ aureus$" refers to a gram-positive, facultative anaerobe that forms cell aggregate (lumps) as it grows, and is generally present in the skin and nasal surface of healthy people or livestock. It produces heat-resistant exotoxin, causing food poisoning, secreting toxins (leukocidin), hemolysin, coagulase, etc. that kill phagocytes, and causing a purulent infectious disease, deviating from the resistance of infected host cells.

In addition, the antimicrobial composition of the present invention is more effective for antibiotic resistant bacteria, and thus it is possible to treat infectious diseases which are difficult to treat with antibiotics. Recently, antibiotic-resistant bacteria showing resistance to most antibiotics have appeared in hospitals and the like, which is causing serious social problems.

The antibiotic-resistant bacterium is a bacterium resistant to the antibiotics, and may be gram-positive bacteria or gram-negative bacteria, preferably gram-positive bacteria.

Examples of the antibiotic-resistant bacteria having the antimicrobial activity of the antimicrobial composition of the present invention include multidrug-resistant $Staphylococcus\ aureus$ (MDRSA), methicillin-resistant $Staphylococcus\ aureus$ (MRSA), vancomycin resistant $Staphylococcus\ aureus$ (VRSA), and vancomycin intermediate $Staphylococcus\ aureus$ (VISA), and preferably multidrug-resistant $Staphylococcus\ aureus$ (MDRSA) or methicillin-resistant $Staphylococcus\ aureus$ (MRSA), but are not limited thereto.

In the present invention, the term "multidrug-resistant $Staphylococcus\ aureus$ (MDRSA)" refers to $Staphylococcus$

*aureus* resistant to a various class of antibiotics as well as methicillin, and is a mutant *bacillus* that has appeared due to the growing use of various antibiotics. It is a bacterium that is resistant to most antibiotics and can only be treated with extremely limited antibiotics.

In the present invention, the term "methicillin-resistant *Staphylococcus aureus* (MRSA)" refers to a *Staphylococcus aureus* resistant to methicillin antibiotics, which are penicillin antibiotics. It is the most frequent causative bacterium among the pathogenic bacteria causing infection in hospitals, and is fatal to patients with impaired immunity or the elderly.

In addition, the antimicrobial composition of the present invention can be used to kill bacteria.

The method of killing the bacteria may be carried out by treating the 7,10-epoxyoctadeca-7,9-dienoic acid of the present invention or treating the 7,10-epoxyoctadeca-7,9-dienoic acid in combination with antibiotics. In case of a combination treatment, the class of antibiotics is not limited. In addition, the method of killing the bacteria is not limited as long as the 7,10-epoxyoctadeca-7,9-dionanoic acid and the antibiotic can be treated at the same time or can be treated separately and sequentially, and the purpose of killing bacteria is achieved.

The present invention also provides a pharmaceutical composition for the prevention or treatment of a bacterial infectious disease comprising the above-antimicrobial composition.

The bacterial infectious diseases may be at least one kind selected from the group consisting of abscess, dermatitis, osteoarthritis, bacteremia, pneumonia, toxic shock syndrome, food poisoning, high fever, sepsis, edema, mastitis and intestinal colibacillosis, but are not limited thereto.

The pharmaceutical composition of the present invention may further include an adjuvant in addition to the 7,10-epoxyoctadeca-7,9-dienoic acid and the antibiotic. Such adjuvants may be used without limitation as long as they are known in the pertinent technical field, but may further include, for example, Freund's complete adjuvant or incomplete adjuvant to increase its immunity.

The pharmaceutical composition according to the present invention may be prepared by incorporating an active ingredient into a pharmaceutically acceptable carrier. Here, the pharmaceutically acceptable carrier includes carriers, excipients and diluents commonly used in the pharmaceutical field. Pharmaceutically acceptable carriers for use in the pharmaceutical composition of the present invention may include, but are not limited to, lactose, dextrose, sucrose, sorbitol, mannitol, xylitol, erythritol, maltitol, starch, acacia rubber, alginate, gelatin, calcium phosphate, calcium silicate, cellulose, methylcellulose, polyvinylpyrrolidone, water, methylhydroxybenzoate, propylhydroxybenzoate, talc, magnesium stearate, and mineral oil.

The pharmaceutical composition of the present invention may be formulated and used as oral preparations such as powders, granules, tablets, capsules, suspensions, emulsions, syrups, and aerosols, external preparations, suppositories or sterilized injection solutions according to a conventional method.

When the pharmaceutical composition is formulated, a formulation may be prepared using a commonly used diluents or excipients such as a filler, an extending agent, a binder, a wetting agent, a disintegrating agent, and a surfactant. A solid formulation for oral administration includes a tablet, a pill, a powder, a granule, a capsule, and the like. Such a solid formulation is prepared by mixing the active ingredients with at least one excipient such as, for example, starch, calcium carbonate, sucrose or lactose, or gelatin. Also, lubricants such as magnesium stearate and talc may be used in addition to the simple excipient. A liquid formulation for oral administration includes a suspension, an internal liquid preparation, an emulsion, and syrup. In general, the liquid formulation may include various excipients, for example, a wetting agent, a sweetening agent, an aromatic, and a preservative in addition to the commonly used diluents such as water and liquid paraffin. A formulation for parenteral administration includes a sterile aqueous solution, a non-aqueous solvent, a suspension, an emulsion, a lyophilized formulation, and a suppository. A vegetable oil such as propylene glycol, polyethylene glycol, or olive oil, and an injectable ester such as ethyl oleate may be used as the non-aqueous solvent and the suspension. Witepsol, Tween 61, cacao butter, laurin butter, or glycerogelatin may be used as a base of the suppository.

The pharmaceutical composition according to the present invention may be administered to a subject via various routes. All modes of administration may be expected, for example, by orally, through intravenous, intramuscular, subcutaneous, or intraperitoneal injection.

The dosage of the pharmaceutical composition according to the present invention is selected in consideration of the age, weight, sex, physical condition, etc. of a subject. It is obvious that the concentration of 7,10-epoxyoctadeca-7,9-dienoic acid (7,10-EODA) included in the pharmaceutical composition may be variously selected depending on the object, and preferably, the pharmaceutical composition may be included in the concentration of 0.01 to 5,000 µg/ml. If the concentration is less than 0.01 µg/ml, the pharmaceutical activity may not be exhibited. If the concentration is more than 5,000 µg/ml, it may be toxic to the human body.

In addition, the present invention provides a cosmetic composition comprising the antimicrobial composition.

The cosmetic composition of the present invention may be variously used for the prevention or improvement of infectious skin diseases. Examples of products to which the present composition may be added include cosmetics such as various creams, lotions, skins, and essences and shampoos, rinses, cleansers, cleansing products, soaps, treatments, packs, essences, and the like.

The cosmetic composition of the present invention may further include a composition selected from the group consisting of a water-soluble vitamin, an oil-soluble vitamin, a high-molecular peptide, a high-molecular polysaccharide, a sphingolipid, and a seaweed extract.

The water-soluble vitamin may be used without limitation as long as it can be blended with cosmetics. Preferably, the water-soluble vitamin may include vitamin B1, vitamin B2, vitamin B6, pyridoxin, pyridoxine hydrochloride, vitamin B12, pantothenic acid, nicotinic acid, nicotinic acid amide, folic acid, vitamin C, or vitamin H. Also, salts (thiamine hydrochloride, ascorbate sodium, etc.) or derivatives (ascorbic acid-2-phosphate sodium, ascorbic acid-2-phosphate magnesium, etc.) of the above-described components may be included in the water-soluble vitamin which may be used in the present invention. The water-soluble vitamin may be obtained using a conventional method such as microbial transformation, purification from a culture solution of a microorganism, enzymatic or chemical synthesis.

The oil-soluble vitamin may be used without limitation as long as it can be blended with cosmetics. Preferably, the water-soluble vitamin may include vitamin A, carotin, vitamin D2, vitamin D3, vitamin E (dl-alpha tocopherol, d-alpha tocopherol, d-alpha tocopherol), and the like. Also, derivatives of the above-described components (ascorbic acid palmitate, ascorbic acid stearate, ascorbic acid dipalmitate, acetic acid dl-alpha tocopherol, nicotinic acid dl-alpha tocopherol vitamin E, DL-pantothenyl alcohol, D-pantothenyl alcohol, pantothenyl ethyl ether, etc.) are included in the oil-soluble vitamin which may be used in the present invention. The oil-soluble vitamin may be obtained using a conventional method such as microbial transformation, purification from a culture solution of a microorganism, enzymatic or chemical synthesis.

The high-molecular peptide may be used without limitation as long as it can be blended with cosmetics. Preferably, the high-molecular peptide may include collagen, hydrolyzed collagen, gelatin, elastin, hydrolyzed elastin, keratin, and the like. The high-molecular peptide may be obtained in a purified form using a conventional method such as purification from a culture solution of a microorganism, enzymatic or chemical synthesis, or be purified from a conventional natural source such as thick skin from pigs or cattle, or fibroin from a silkworm.

The high-molecular polysaccharide may be used without limitation as long as it can be blended with cosmetics. Preferably, the high-molecular polysaccharide may include hydroxyethyl cellulose, xanthan gum, sodium hyaluronate, chondroitin sulfate or salts thereof (sodium salt, etc.). For example, chondroitin sulfate or a salt thereof may be generally purified from a mammal or a fish.

The sphingolipid may be used without limitation as long as it can be blended with cosmetics. Preferably, the sphingolipid may include ceramide, phytosphingosine, glycosphingolipid, and the like. The sphingolipid may be generally purified from a mammal, a fish, a shellfish, yeast, or a plant using a conventional method, or obtained using a conventional method such as chemical synthesis.

The seaweed extract may be used without limitation as long as it can be blended with cosmetics. Preferably, the seaweed extract may include a brown alga extract, a red alga extract, a green alga extract, and the like. Also, carrageenan, alginic acid, sodium alginate, potassium alginate, and the like purified from the seaweed extracts are included in the seaweed extract used in the present invention. The seaweed extract may be obtained from seaweed using a conventional method such as purification.

In addition to the essential components, the cosmetic composition of the present invention may include other components that may be blended into a conventional cosmetic composition, when necessary. In addition to the above-described components, a blending component which may be added herein may include a fat component, a humectant, an emollient, a surfactant, organic and inorganic pigments, an organic powder, a UV absorber, an antiseptic, a bactericide, an antioxidant, an herbal extract, a pH regulating agent, an alcohol, a coloring matter, an aromatic, a blood flow stimulant, a cooling agent, an antiperspirant, purified water, and the like. The fat component may include ester-based fat, hydrocarbon-based fat, silicon-based fat, fluorine-based fat, animal fat, vegetable fat, and the like.

The ester-based fat may include tri-2-ethylhexaneglyceryl, 2-ethylhexanecetyl, myristic acid isopropyl, myristic acid butyl, palmitic acid isopropyl, stearic acid ethyl, palmitic acid octyl, isostearic acid isocetyl, stearic acid butyl, linoleic acid ethyl, linoleic acid isopropyl, oleic acid ethyl, myristic acid isocetyl, myristic acid isostearyl, palmitic acid isostearyl, myristic acid octyldodecyl, isostearic acid isocetyl, sebacic acid diethyl, adipic acid diisopropyl, neopentanoic acid isoalkyl, tri(caprylic, capric acid)glyceryl, tri-2-ethylhexanetrimethylolpropane, triisostearic acid trimethylolpropane, tetra-2-ethylhexanepentaerythritol, caprylic acid cetyl, lauric acid decyl, lauric acid hexyl, myristic acid decyl, myristic acid myristyl, myristic acid cetyl, stearic acid stearyl, oleic acid decyl, ricinoleic acid cetyl, lauric acid isostearyl, myristic acid isotridecyl, palmitic acid isocetyl, stearic acid octyl, stearic acid isocetyl, oleic acid isodecyl, oleic acid octyldodecyl, linoleic acid octyldodecyl, isostearic acid isopropyl, 2-ethylhexanecetostearyl, 2-ethylhexanestearyl, isostearic acid hexyl, dioctanoic acid ethyleneglycol, dioleic acid ethyleneglycol, dicapric acid propylene glycol, di(caprylic, capric acid) propylene glycol, dicaprylic acid propylene glycol, dicapric acid neopentylglycol, dioctanoic acid neopentylglycol, tricaprylic acid glyceryl, triundecylic acid glyceryl, triisopalmitic acid glyceryl, triisostearic acid glyceryl, neopentanoic acid octyldodecyl, octanoic acid isostearyl, isononanoic acid octyl, neodecanoic acid hexyldecyl, neodecanoic acid octyldodecyl, isostearic acid isocetyl, isostearic acid isostearyl, isostearic acid octyldecyl, polyglycerineoleic acid ester, polyglycerineisostearic acid ester, citric acid triisocetyl, citric acid triisoalkyl, citric acid triisooctyl, lactic acid lauryl, lactic acid myristyl, lactic acid cetyl, lactic acid octyldecyl, citric acid triethyl, citric acid acetyltriethyl, citric acid acetyltributyl, citric acid trioctyl, malic acid diisostearyl, hydroxystearic acid 2-ethylhexyl, succinic acid di-2-ethylhexyl, adipic acid diisobutyl, sebacic acid diisopropyl, sebacic acid dioctyl, stearic acid cholesteryl, isostearic acid cholesteryl, hydroxystearic acid cholesteryl, oleic acid cholesteryl, oleic acid dihydrocholesteryl, isostearic acid phytosteryl, oleic acid phytosteryl, 12-stearoylhydroxystearic acid isocetyl, 12-stearoylhydroxystearic acid stearyl, 12-stearoylhydroxystearic acid isostearyl, and the like.

The hydrocarbon-based fat may include squalene, liquid paraffin, α-olefin oligomer, isoparaffin, ceresin, paraffin, liquid isoparaffin, polybutene, microcrystalline wax, Vaseline, and the like.

The silicon-based fat may include polymethylsilicon, methylphenylsilicon, methylcyclopolysiloxane, octamethylpolysiloxane, decamethylpolysiloxane, dodecamethylcyclosiloxane, a dimethylsiloxane/methylcetyloxysiloxane copolymer, a dimethylsiloxane/methylstearoxysiloxane copolymer, alkyl-modified silicon oil, amino-modified silicon oil, and the like.

The fluorine-based fat may include perfluoropolyether, and the like.

The animal or vegetable fat may include avocado oil, almond oil, olive oil, sesame oil, rice bran oil, safflower oil, soybean oil, corn oil, rapeseed oil, apricot oil, palm kernel oil, palm oil, castor oil, sunflower oil, grape seed oil, cottonseed oil, coconut oil, kukui nut oil, wheat germ oil, rice germ oil, shea butter, evening primrose oil, macadamia nut oil, meadowfoam oil, egg yolk oil, tallow, horse oil, mink oil, orange roughy oil, jojoba oil, candelilla wax, carnauba wax, liquid lanolin, hydrogenated castor oil, and the like.

The humectant may include a water-soluble low-molecular humectant, a fat-soluble low-molecular humectant, a water-soluble polymer, a fat-soluble polymer, and the like.

The water-soluble low-molecular humectant may include serine, glutamine, sorbitol, mannitol, pyrrolidone-sodium carboxylate, glycerine, propylene glycol, 1,3-butyleneglycol, ethyleneglycol, polyethyleneglycol B (degree of polymerization (n) of at least 2), polypropylene glycol (degree of polymerization (n) of at least 2), polyglycerine B (degree of polymerization (n) of at least 2), lactic acid, lactate, and the like.

The fat-soluble low-molecular humectant may include cholesterol, cholesterolester, and the like.

The water-soluble polymer may include carboxyvinyl polymer, polyaspartate, tragacanth, xanthan gum, methyl cellulose, hydroxymethylcellulose, hydroxyethyl cellulose, hydroxypropyl cellulose, carboxymethyl cellulose, water-soluble chitin, chitonic acid, dextrin, and the like.

The fat-soluble polymer may include a polyvinylpyrrolidone/eicosene copolymer, a polyvinylpyrrolidone/hexadecene copolymer, nitrocellulose, dextrin fatty acid ester, polymer silicon, and the like. The emollient may include long-chain acyl glutamic acid cholesteryl ester, hydroxystearic acid cholesteryl, 12-hydroxystearic acid, stearic acid, rosin acid, lanolin fatty acid cholesteryl ester, and the like.

The surfactant may include a non-ionic surfactant, an anionic surfactant, a cationic surfactant, an amphoteric surfactant, and the like.

The non-ionic surfactant may include self-emulsified monostearic acid glycerine, propylene glycol fatty acid ester, glycerine fatty acid ester, polyglycerine fatty acid ester, sorbitan fatty acid ester, polyoxyethylene (POE) sorbitan fatty acid ester, POE sorbite fatty acid ester, POE glycerine fatty acid ester, POE alkylether, POE fatty acid ester, POE hydrogenated castor oil, POE castor oil, a POE/polyoxypropylene (POP) copolymer, POE/POP alkylether, polyether-modified silicon, lauric acid alkanol amide, alkylamine oxide, hydrogenated soybean phospholipid, and the like.

The anionic surfactant may include fatty acid soap, α-acylsulfonate, alkylsulfonate, alkylarylsulfonate, alkylnaphthalenesulfonate, alkylsulfate, POE alkylethersulfate, alkylamidesulfate, alkylphosphate, POE alkylphosphate, alkylamidephosphate, alkyloylalkyltaurate, N-acylamino acid salt, POE alkylethercarboxylate, alkylsulfosuccinate, sodium alkylsulfoacetate, acylated hydrolyzed collagen peptide salt, perfluoroalkyl phosphate ester, and the like.

The cationic surfactant may include alkyltrimethyl ammonium chloride, stearyltrimethyl ammonium chloride, stearyltrimethyl ammonium bromide, cetostearyltrimethyl ammonium chloride, distearyldimethyl ammonium chloride, stearyldimethylbenzyl ammonium chloride, behenyltrimethyl ammonium bromide, benzalkonium chloride, diethylaminoethylamide stearate, dimethylaminopropylamide stearate, quaternary ammonium derivatives of lanolin, and the like.

The amphoteric surfactant may include carboxybetaine-type, amide betaine-type, sulfobetaine-type, hydroxyl sulfobetaine-type, amide sulfobetaine-type, phosphobetaine-type, aminocarboxylate-type, imidazoline derivative-type, amideamine-type amphoteric surfactants, and the like.

The organic and inorganic pigment may include an inorganic pigment such as silicic acid, silica, magnesium silicate, talc, sericite, mica, kaolin, bengala, clay, bentonite, titan-coated mica, bismuth oxychloride, zirconium oxide, magnesium oxide, zinc oxide, titanium oxide, aluminium oxide, calcium sulfate, barium sulfate, magnesium sulfate, calcium carbonate, magnesium carbonate, iron oxide, ultramarine, chromium oxide, chromium hydroxide, calamine, and a complex thereof; an organic pigment such as polyamide, polyester, polypropylene, polystyrene, polyurethane, vinyl resin, urea resin, phenol resin, fluorine resin, silica resin, acrylic resin, melamine resin, epoxy resin, polycarbonate resin, a divinylbenzene/styrene copolymer, silk powder, cellulose, CI Pigment Yellow, or CI Pigment Orange; and a complex pigment of the inorganic pigment and the organic pigment, and the like.

The organic powder may include a metallic soap such as calcium stearate; a metal alkylphosphate such as zinc sodium cetylate, zinc laurylate, or calcium laurylate; a polyvalent acylamino acid metal salt such as N-lauroyl-β-alanine calcium, N-lauroyl-β-alanine zinc, or N-lauroyl glycine calcium; a polyvalent amide sulfonic acid metal salt such as N-lauroyl-taurine calcium or N-palmitoyl-taurine calcium; a N-acyl basic amino acid such as N-ε-lauroyl-L-lysine, N-ε-palmitoyllysine, N-α-palmitoyl ornithine, N-α-lauroylarginine, or N-α-hydrogenated tallow fatty acid acyl arginine; an N-acylpolypeptide such as N-lauroylglycylglycine; an α-amino fatty acid such as α-amino caprylic acid, or α-amino lauric acid; polyethylene, polypropylene, nylon, polymethylmethacrylate, polystyrene, a divinylbenzene/styrene copolymer, tetrafluoroethylene, and the like.

The UV absorber may include para-amino benzoic acid, ethyl-para-aminobenzoate, amyl-para-aminobenzoate, octyl-para-aminobenzoate, salicylic acid ethylene glycol, phenyl salicylate, octyl salicylate, benzyl salicylate, butylphenyl salicylate, homomentyl salicylate, benzyl cinnamate, 2-ethoxyethyl para-methoxy cinnamate, octyl para-methoxy cinnamate, mono-2-ethyl hexane glyceryl di-para-methoxy cinnamate, isopropyl para-methoxy cinnamate, a diisopropyl/diisopropyl cinnamic acid ester mixture, urocanic acid, ethyl urocanate, hydroxy methoxybenzophenone, hydroxyl methoxybenzophenone sulfonic acid and slats thereof, dihydroxy methoxybenzophenone, sodium dihydroxy methoxybenzophenone disulfonate, dihydroxy benzophenone, tetrahydroxy benzophenone, 4-tert-butyl-4'-methoxy dibenzoylmethane, 2,4,6-trianilino-p-(carbo-2'-ethylhexyl-1'-oxy)-1,3,5-triazine, 2-(2-hydroxy-5-methylphenyl)benzotriazole, and the like.

The bactericide may include hinokitiol, triclosan, trichlorohydroxydiphenyl ether, chlorhexidine gluconate, phenoxy ethanol, resorcin, isopropylmethylphenol, azulene, salicylic acid, zinc pyrithione, benzalkonium chloride, photosensitizer 301, sodium mononitroguaiacol, undecylenic acid, and the like.

The antioxidant may include butylhydroxy anisole, propyl gallate, erythorbic acid, and the like.

The pH regulating agent may include citric acid, sodium citrate, malic acid, sodium malate, fumaric acid, sodium fumarate, succinic acid, sodium succinate, sodium hydroxide, disodium hydrogen phosphate, and the like.

The alcohol may include a higher alcohol such as cetyl alcohol.

In addition, a blending component which may be added herein is not limited to the above-described components, and any component may be blended in such a range that the objects and effects of the present invention are not hindered.

The cosmetic composition of the present invention may be prepared in the form of solution, emulsion, or viscous mixture.

The components included in the cosmetic composition of the present invention may further include components generally used for a cosmetic composition as active ingredients. For example, the cosmetic composition includes a conventional adjuvant and carrier such as a stabilizing agent, a solubilizing agent, a vitamin, a pigment, and an aromatic.

The cosmetic composition for skin whitening and anti-aging of the present invention may be prepared into any formulation which is generally prepared in the art, and examples of the formulation may include a milky lotion, a cream, a face lotion, a pack, a foundation lotion, a lotion, an essence, a hair care composition, and the like.

Specifically, the cosmetic composition of the present invention may include formulations such as a skin lotion, a skin softener, a skin toner, a milk lotion, an astringent, a lotion, a moisturizing lotion, a nutrition lotion, a massage cream, a nutrition cream, a moisturizing cream, a hand cream, a pack, a soap, a cleansing foam, a cleansing lotion, a cleansing cream, a hair lotion, a hair tonic, a hair essence, a hair shampoo, a hair conditioner, a hair treatment, a body lotion, and a body cleanser.

When a formulation of the present invention is in the form of a paste, cream or gel, an animal fiber, a vegetable fiber, a wax, paraffin, a starch, tragant, a cellulose derivative, polyethylene glycol, silicon, bentonite, silica, talc, or zinc oxide may be used as a carrier component.

When the formulation of the present invention is in the form of a powder or spray, lactose, talc, silica, aluminum hydroxide, calcium silicate, or polyamide powder may be used as the carrier component. Particularly, when the formulation of the present invention is in the form of spray, the formulation may further include a propellent such as chlorofluorohydrocarbon, propane/butane or dimethylether.

When the formulation of the present invention is in the form of a solution or emulsion, a solvent, a solvating agent or an emulsifying agent may be used as the carrier component. For example, the carrier component may include water, ethanol, isopropanol, ethyl carbonate, ethyl acetate, benzyl alcohol, benzyl benzoate, propylene glycol, 1,3-butylglycol oil, aliphatic glycerol ester, polyethylene glycol, or sorbitan fatty acid ester.

When the formulation of the present invention is in the form of a suspension, a liquid diluent such as water, ethanol or propylene glycol, suspensions such as ethoxylated isostearyl alcohol, polyoxyethylene sorbitol ester, and polyoxyethylene sorbitan ester, microcrystalline cellulose, aluminum methahydroxide, bentonite, agar, or tragant may be used as the carrier component.

When the formulation of the present invention is in the form of surfactant-containing cleansing, aliphatic alcohol sulfate, aliphatic alcohol ether sulfate, sulfosuccinic acid monoester, isethionate, imidazolium derivative, methyltaurate, sarcosinate, fatty acid amide ether sulfate, alkylamido betaine, aliphatic alcohol, fatty acid glyceride, fatty acid diethanolamide, a vegetable oil, a linolin derivative, or ethoxylated glycerol fatty acid ester may be used as the carrier component.

The present invention also provides a food composition comprising the antimicrobial composition.

The food composition comprising the antimicrobial composition of the present invention may be used as a health functional food, a food additive, or a dietary supplement.

When the food composition comprising the antimicrobial composition is used as a food additive, it can be suitably used according to a conventional method such as adding it directly or mixing it with another food or food ingredient.

In addition, the amount of 7,10-epoxyoctadeca-7,9-dienoic acid included in the food composition or the mixing amount of 7,10-epoxyoctadeca-7,9-dienoic acid and the antibiotics may be appropriately changed according to the purpose of uses (prevention, health or therapeutic treatment). That is, it may be preferably included in an amount of 0.01 to 95% by weight, and more preferably an amount of 0.1 to 80% by weight, based on the total weight of the food composition. If the content is less than 0.01% by weight, the efficiency of doses may be lowered. If the content is more than 80% by weight, formulation may be difficult.

As a specific example, at the time of preparing food or beverage, the amount of 7,10-epoxyoctadeca-7,9-dienoic acid of the present invention or the amount of 7,10-epoxyoctadeca-7,9-dienoic acid and antibiotics of the present invention is added in an amount of not more than 15% by weight, preferably not more than 10% by weight based on the raw material. However, in case of long-term intake for health and hygiene purposes or for the purpose of controlling health, it may be added in an amount equal to or less than the above range, and since there is no problem in safety, the active ingredient may be used in an amount equal to or higher than the above range.

There is no particular limitation on the kind of the food. Examples of the foods to which the food composition of the present invention may be added include meat, sausage, bread, chocolate, candy, snacks, confectionery, pizza, ramen, other noodles, gums, dairy products including ice cream, various soups, beverages, tea, drinks, alcoholic beverages, and vitamin complexes, all of which include healthy foods in the conventional sense.

When the food composition of the present invention is prepared as a beverage, it may include an additional component such as various flavoring agents or natural carbohydrates, like a conventional beverage. Examples of the above-described natural carbohydrates include a monosaccharide such as glucose, fructose, a disaccharide such as maltose or sucrose, a natural sweetening agent such as dextrin, cyclodextrin, and a synthetic sweetening agent such as saccharin, and aspartame. The natural carbohydrate may be present in a content of 0.01 to 10% by weight, and preferably 0.01 to 0.1% by weight, based on the total weight of the food composition of the present invention.

The food composition of the present invention may include a variety of nutrients, a vitamin, an electrolyte, a flavoring agent, a coloring agent, pectic acid and salts thereof, alginic acid and salts thereof, organic acid, a protective colloidal thickener, a pH regulating agent, a stabilizing agent, an antiseptic, glycerine, alcohol, and a carbonating agent used in a carbonated beverage. In addition, the compositions may include a pulp for preparation of natural fruit juice, fruit juice beverage, and vegetable juice, but are not limited thereto. These components may be used alone or in combination. The proportion of the above additives is not particularly limited, but is preferably within a range of 0.01 to 0.1% by weight based on the total weight of the food composition of the present invention.

For long-term intake intended for health and hygiene purposes or health control purposes, the food composition of the present invention has no problem in terms of safety and thus can be taken for a long period of time.

The present invention also provides an animal feed composition comprising the antimicrobial composition.

The amount of 7,10-epoxyoctadeca-7,9-dienoic acid or the mixing amount of 7,10-epoxyoctadeca-7,9-dienoic acid and antibiotics included in the animal feed composition is preferably included in an amount of 0.01 to 95% by weight, and more preferably an amount of 0.1 to 80% by weight, based on the total weight of the animal feed composition. If the content is less than 0.01% by weight, the efficiency of doses may be lowered. If the content is more than 95% by weight, formulation may be difficult.

The animal feed composition can prevent or improve an infectious disease caused by pathogenic bacteria in an animal by feeding the livestock.

The target animal to which the animal feed composition is administered may be both ruminant and non-ruminant, but preferably it may be a ruminant, and the species may be cattle, camels, deer, giraffe, and the like.

The animal feed composition of the present invention may further include organic acids such as citric acid, fumaric acid, adipic acid, lactic acid, and malic acid, phosphates such as sodium phosphate, potassium phosphate, acid pyrophosphate, and polyphosphate (polymerized phosphate), or natural antioxidants such as polyphenol, catechin, alpha-tocopherol, rosemary extract, vitamin C, green tea extract, licorice extract, chitosan, tannic acid, and phytic acid.

In addition, the animal feed composition may further include auxiliary components such as amino acids, inorganic salts, vitamins, antibiotics, antimicrobials, antioxidants, antifungal enzymes, viable microbial preparations and the like. Specifically, examples of the auxiliary component may include cereals (e.g., ground or crushed wheat, oats, barley, corn, rice, and the like), vegetable protein feed (e.g., those having rape, soybean, sunflower as main components), animal protein feed (e.g., blood meal, meat meal, bone meal, fish powder, etc.), sugar and dairy products (e.g., dry ingredients including various powdered milk or whey powders), lipids (e.g., animal fat, vegetable fat, etc.), nutritional supplements, digestion and absorption enhancers, growth promoters, disease prevention agents, and the like.

The animal feed composition may be administered alone to an animal or may be administered in mixture with other feed additives in an edible carrier. In addition, the animal feed composition may be mixed with the top dressing of the feed, or may be easily administered in combination with feeds, separate additives, or separate oral formulations. The dosage of the animal feed composition can be suitably adjusted by using a single daily intake or a divided daily intake commonly administered in the art.

The present invention also provides a disinfectant comprising the antimicrobial composition.

In addition, the present invention provides an antimicrobial adjuvant for the killing of an antibiotic resistant bacterium comprising the antimicrobial composition.

Hereinafter, it will be apparent to a person having ordinary skill in the technical field to which the present invention pertains that the examples are for illustrative purposes only in more details and that the scope of the present invention is not construed as being limited by these examples without departing from gist of the present invention.

Experimental Example 1. Preparation of 7,10-epoxyoctadeca-7,9-dienoic acid (7,10-EODA)

10 mg of 7,10-dihydroxy-8(E)-octadecenoic acid (DOD) and 500 µl of hexane as a solvent were placed in 4 ml glass vials and reacted in a heating block (Barnstead/Thermolyne Type 176000 Dry-Bath) at 95° C. for 24 hours. After completion of the reaction, the solvent was removed using nitrogen flushing, and the reaction product was dissolved in a mixture of chloroform and methanol (1:1, v/v) to obtain a product.

The structure of the resultant product was confirmed by thin layer chromatography, gas chromatography, gas chromatography/mass spectrometry, and the like. Thin layer chromatography was performed on a glass substrate coated with silica gel. The solvent for the separation of the product was a mixture of toluene: Dioxan:Acetic acid (79:14:7, v/v/v). After the product was separated, the product was confirmed by spots shown after 50% solution of sulfuric acid was sprayed on the substrate and heated at 100° C. for 10 minutes. Gas chromatographic analysis was carried out by adding 1 ml of diazomethane to 10 mg of the sample to be analyzed and then allowing to stand at room temperature for 5 minutes. Diazomethane was removed using nitrogen gas, and 1 ml of TMSI+ Pyridine (1:4, v/v) was added and left for 40 minutes. After the residual solvent was blown off with nitrogen gas, 200 µl of a solution for gas chromatography (Dichrolomethane:Methanol=95:5, v/v) was added. 1 µl of the final sample thus prepared was injected into a gas chromatographic spectrometer. At this time, the column used was a hydrophobic column, the analysis temperature was in the range of 100° C. to 300° C., and the analysis time was within 1 hour. The gas chromatography/mass spectrometer was analyzed in accordance with the gas chromatography method, and a column having a length of 30 m or more was used, and a mass spectrometer was installed and performed in a detector of the separated molecules. The structure of the product identified by the method was 7,10-epoxyoctadeca-7,9-dienoic acid (7,10-EODA), in which on a $C_{18}$ fatty acid chain, carbons 7 and 10 are linked by an epoxy structure, and a furan ring composed of carbons 7, 8, 9, and 10 is formed. The reaction proceeds as shown in Reaction Scheme 1 below.

[Reaction Scheme 1]

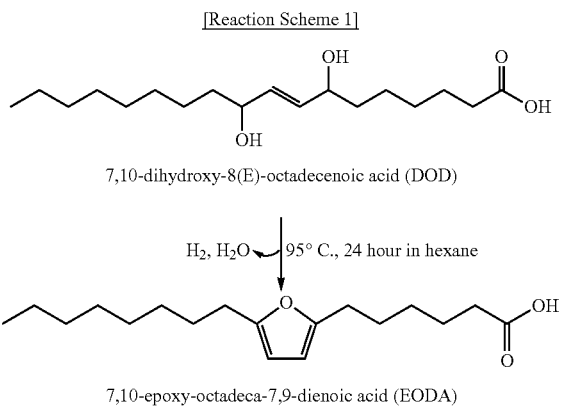

7,10-dihydroxy-8(E)-octadecenoic acid (DOD)

$H_2$, $H_2O$ ↓ 95° C., 24 hour in hexane 7,10-epoxy-octadeca-7,9-dienoic acid (EODA)

Experimental Example 2. Bacteria and Culture Conditions

MDRSA 01ST001 and MRSA strains 02ST085, 01ST093, 02ST165, and 02ST136, which are strains of multidrug-resistant *Staphylococcus aureus* (MDRSA), which are clinically isolated and deposited in the National Culture Collection for Pathogens, were provided from Kyungbook National University Hospital Branch of National Culture Collection for Pathogens. The strains were tested for the presence of pbp2a by Oxoid latex agglutination assay. Methicillin-sensitive *S. aureus* (ATCC 29213) and *Escherichia coli* (ATCC 8739) were obtained from ATCC (American Type Culture Collection, Baltimore, USA). *S. aureus* 1199 (clinical isolation) was obtained from Wayne State University (MI, USA) and *Salmonella typhimurium* (KCTC 2515) was obtained from KCTC (Korean Collection for Type Cultures). All bacterial strains were cultured in TSB (trypticase soy broth) or NB (nutrient broth) medium purchased from Becton Dickinson (Cockeysville, Md., USA) and stored at −80° C. in NB medium containing 25% glycerol. It was cultured overnight at the optimum temperature condition and used for the experiment.

Experimental Example 3. Reagents and Substances

Antibiotics, chemicals, and solvents used in the present invention were purchased from Sigma Aldrich (St. Louis, Mo., USA). All analytical grade chemicals and reagents were used. The furan fatty acid 7,10-EODA was prepared by using the 7,10-EODA prepared in Experimental Example 1 and having a purity of 95% or more by gas chromatography.

Experimental Example 4. Measurement of Minimal Inhibitory Concentration (MIC)

The minimum inhibitory concentration (MIC) of antibiotics and the activity of 7,10-EODA of the present invention against Staphylococcus aureus strains were measured according to the CLSI guideline (CLSI document M100-517, 2007). Specifically, each antibiotic or 7,10-EODA was diluted 2-fold (200-0.97 µg/mL) by adding MHB (Mueller-Hinton Broth) to a 96-well microtiter plate. In the mid-exponential phase (0.5 $OD_{600}$), the culture was diluted 10-fold with MHB and 0.1 mL aliquots of the diluent were added to wells containing the serially diluted test reagent and cultured at 37° C. for 12 hours. About the end of the culture period, the cell density was measured at an optical density of 600 nm ($OD_{600}$) using a culture medicine. The minimum concentration required to prevent proliferation (90% or higher relative to a control group) was regarded as MIC and was confirmed.

Experimental Example 5. Synergy Effect Screening by Agar Disk Diffusion Analysis For synergy effect screening, a 0.1 mL aliquot of MRSA or MSSA strain ($5\times10^5$ CFU/mL) cultured in a log-phase on TSA plates was inoculated. Thereafter, two sets of sterile filter paper disks were placed on an agar plate, while one set including the antibiotic (¼×MIC) was impregnated and the other set including the 7,10-EODA (¼×MIC) was impregnated with the antibiotic. A disk including DMSO alone or 7,10-EODA alone (¼×MIC) was used as a control group. The plates were cultured under conditions of 27° C. and 24 hours, and a synergistic effect was observed when the disk periphery including both antibiotic and 7,10-EODA was at least 5 mm in zone of inhibition (ZOI).

Experimental Example 6. Evaluation of Synergy Effect

Interactions of the selected antibiotic or 7,10-EODA of the present invention were evaluated using the checker board method (Nair et al. 2015). A 2-fold dilution of the serially diluted 7,10-EODA from 250 µg/mL (2×MIC) stock was prepared in a 96-well microtiter plate column. To obtain various concentrations of 7,10-EODA and antibiotic combination, a 2-fold dilution of the beta-lactam antibiotic was placed on the same plate. About $10^5$ CFU/mL of microorganisms to be tested was added to the wells of each plate, and cultured for 24 hours at 37° C. without shaking. At the end of the culture period, cell growth was measured at $OD_{600}$ using a spectrophotometer. Each 7,10-EODA and antibiotic combination was repeated at least three times. MIC was identified at the lowest concentration of antibiotics with growth inhibition of 90% or higher. $FIC_{AB}$ means fractional inhibitory concentration (FIC) of drug A in the presence of drug B, and $FIC_{BA}$ means fractional inhibitory concentration (FIC) of drug B in the presence of drug A. The fractional inhibitory concentration index (FICI) represents the sum of the FIC values of the interacting antibiotics. Interactions are based on FICI values, with FICIs less than 0.5 being categorized as synergy, FICIs 0.5 to 4 being indifferent, and FICIs greater than 4 being antagonistic. The degree of synergy was also measured based on the conventional Bliss independence model of synergy (Morones-Ramirez et al. 2013). Specifically, the degree of synergy was calculated by the following equation: S indicates degree of synergy, $f_{AB}$ indicates bacterial growth (optical density) when 7,10-EODA and antibiotics are used in combination, $f_{A0}$ and $f_{0B}$ represent bacterial growth for antibiotic alone or 7,10-EODA single treatment, respectively. $f_{00}$ represents bacterial growth in the absence of drug. The degree of synergy is divided into three categories based on the S value, where 0 means neutral, greater than 0 means synergism, and less than 0 means antagonism.

$$S=(f_{A0}/f_{00})(f_{0B}/f_{00})-(f_{AB}/f_{00})$$

Experimental Example 7. Time-Kill Assay

Synergy interrelationships between 7,10-EODA and antibiotics were measured by changes in viability in time-kill analysis. In a glass tube containing 1 mL of MHB and containing the antibiotic single group (¼×MIC), 7,10-EODA single group (¼×MIC) or the combination group of 7,10-EODA and antibiotics, MRSA (about $10^5$ CFU/mL) was included and cultured. One that cultured only MHB was used as a control group. It was cultured in a shaking incubator (150 rpm) at 37° C. for 24 hours. At $0^{th}$, $4^{th}$, $8^{th}$ and $24^{th}$ hours, 0.1 mL aliquots were removed from the culture, and the cells were continuously diluted and cultured at 37° C. for 24 hours on a plate containing MHA (Mueller-Hinton Agar). Survival colonies for each treatment group were counted and expressed as log CFU/mL relative to incubation time. Each treatment group was repeated three times and expressed as mean±SD. A lower number of surviving colonies than 2.5 log CFU was considered as a synergy interaction (Lorian, 2005, Lippincott Williams & Wilkins, Philadelphia).

Example 1

Confirmation of Antimicrobial Activity of 7,10-epoxyoctadeca-7,9-dienoic acid (EODA) Against Methicillin Resistant Staphylococcus aureus To confirm the antimicrobial activity of 7,10-epoxyoctadeca-7,9-dienoic acid (7,10-EODA), the antimicrobial activity against methicillin resistant Staphylococcus aureus (MRSA) 01ST001, an antibiotic resistant bacterium, was confirmed by using the solid medium.

First, 1.5% of potato agar was added to the YDP medium, sterilized, and then an agar plate hardened by pouring about 20 ml in a plastic Petri dish was used. MRSA 01ST001 was diluted to about 107/ml, and then about 500 µl was dispersed evenly on the agar plate.

Then, the prepared filter paper having a diameter of about 5 mm was placed on an agar plate inoculated with MRSA 01ST001, and 7,10-epoxyoctadeca-7,9-dienoic acid (7,10-EODA) was inoculated on the filter paper at concentrations of 50, 100, 200, and 400 µg. The size of the clear zone around the filter paper shown after the culture at 37° C. for 2 to 3 days after the inoculation was measured to confirm the degree of antimicrobial activity. At this time, vancomycin 100 µg, oxacillin 100 µg, ampicillin 100 µg, streptomycin 100 µg, and penicillin 100 µg were used as control groups.

The antimicrobial activity can be confirmed with the degree showing the clear zone on the agar plate. It is judged that the larger the clear zone, the higher the antimicrobial activity. The results are illustrated in FIG. 1 and FIG. 2.

Spots A to E in FIG. 1 were obtained by treating conventional antibiotics, spot F was treated with 7,10-epoxyoctadeca-7,9-dionanoic acid (7,10-EODA), and all the treatment samples were treated at the same concentration of 100 µg. As illustrated in FIG. 1, a clear zone appeared in the vancomycin-treated spot, but no clear zone appeared in the case of oxacillin, ampicillin, streptomycin, and penicillin. That is, only vancomycin, which exhibits antimicrobial activity against the microorganism strain MRSA used in the experiment, showed a clear zone. On the other hand, vancomycin is currently known as a commercial antibiotic that can inhibit the growth of MRSA, but it is highly toxic and is severely limited in its use.

However, it has been confirmed that a clear zone similar in size to vancoclin is formed in the case of 7,10-epoxyoctadeca-7,9-dienoic acid (7,10-EODA) (spot F) which is an active ingredient of the present invention. From these results, it was confirmed that 7,10-epoxyoctadeca-7,9-dienoic acid (7,10-EODA) showed a high antimicrobial activity against MRSA which is a multidrug-resistant *Staphylococcus aureus*.

Figure 2:
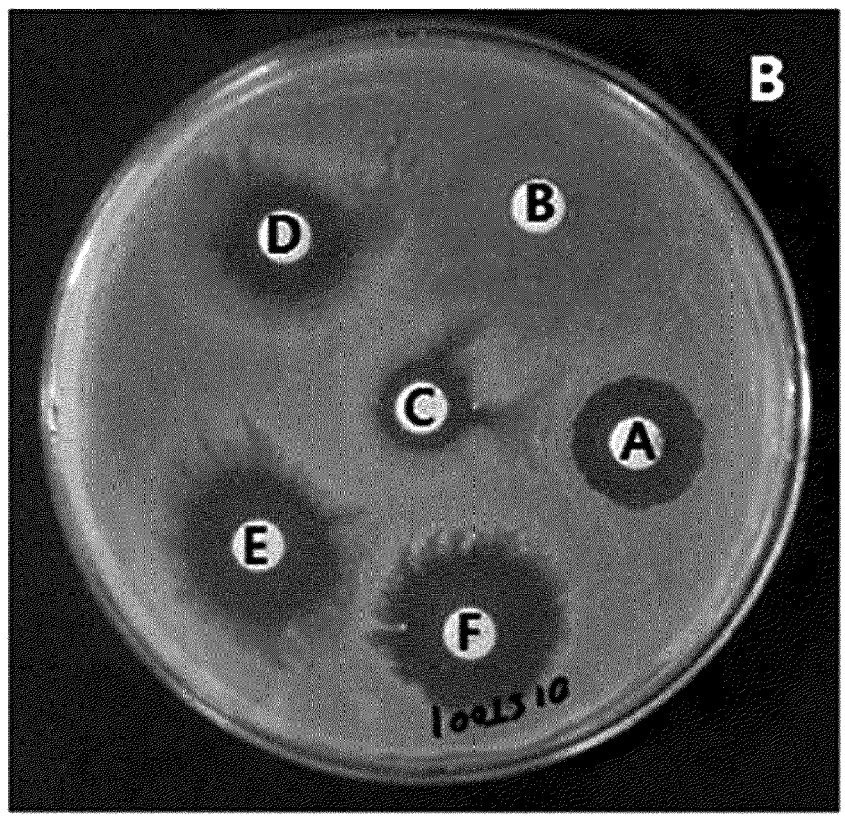
FIG. 2 is a diagram illustrating the results of confirming that 7,10-EODA exhibits enhanced antimicrobial activity in a concentration-dependent manner by treating 7,10-epoxyoctadeca-7,9-dienoic acid (7,10-EODA) with different concentrations of multidrug-resistant *Staphylococcus* (MDRSA 01ST001).

FIG. 2 also illustrates the results of an experiment in which MRSA 01ST001 was treated with 7,10-epoxyoctadeca-7,9-dienoic acid (7,10-EODA) at different concentrations. It was confirmed that as the treatment concentration of 7,10-epoxyoctadeca-7,9-dienoic acid (7,10-EODA) was increased, the size of the clear zone was increased. From these results, it was found that 7,10-epoxyoctadeca-7,9-dienoic acid (7,10-EODA), which is an active ingredient of the present invention, showed an antimicrobial activity which was improved in a concentration-dependent manner. Therefore, methicillin resistant *Staphylococcus aureus* (MRSA) 01ST001 is hereinafter referred to as multidrug-resistant *Staphylococcus aureus* (MDRSA) 01ST001.

Example 2

Confirmation of the Antimicrobial Activity of 7,10-epoxyoctadeca-7,9-dienoic acid (7,10-EODA) Against Common *Staphylococcus*

Figure 3:
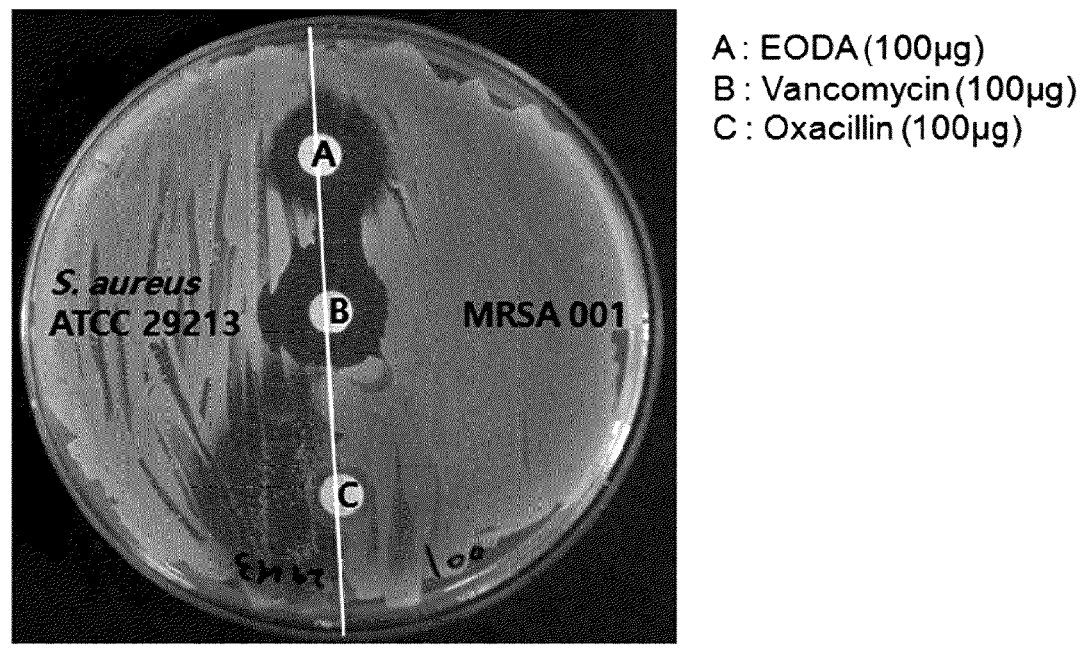
FIG. 3 is a diagram illustrating the results of comparing the antimicrobial activity of 7,10-epoxyoctadeca-7,9-dienoic acid (7,10-EODA) against common *Staphylococcus* and multidrug-resistant *Staphylococcus* (MDRSA 01ST001) using a solid medium according to one embodiment of the present invention.

7,10-epoxyoctadeca-7,9-dienoic acid (7,10-EODA) was used to compare the antimicrobial activity against *Staphylococcus aureus* ATCC 29213, a common *Staphylococcus*, and MDRSA 01ST001, a multidrug-resistant *Staphylococcus aureus*, an antibiotic resistant bacterium. The results are illustrated in FIG. 3. The experiment was carried out in the same manner as in Example 1-2.

As illustrated in FIG. 3, it was confirmed that vancomycin exhibited the same antimicrobial activity against common *Staphylococcus* and multidrug-resistant antibiotic resistant bacteria MDRSA, and oxacillin showed a high antimicrobial activity against *Staphylococcus aureus* ATCC 29213, a common *Staphylococcus*, but did not show an antimicrobial activity against MDRSA 01ST001. On the other hand, in the case of 7,10-epoxyoctadeca-7,9-dienoic acid (7,10-EODA) as an active ingredient of the present invention, the antimicrobial activity was exhibited for both strains. In particular, it was confirmed that MDRSA 01ST001, which is a multidrug-resistant antibiotic resistant bacterium, has a higher antimicrobial activity than *Staphylococcus aureus* ATCC 29213, which is a common *Staphylococcus*.

Example 3

Antimicrobial Activity Synergistic Effect of 7,10-EODA on Multidrug-Resistant *Staphylococcus aureus* (MDRSA)

The synergistic effect of the 7,10-EODA of the present invention on the multidrug-resistant *Staphylococcus aureus* (MDRSA) strain 01ST001 was confirmed.

Specifically, in order to compare the antimicrobial activity of the 7,10-EODA or the antibiotic of the present invention against the MDRSA 01ST001 strain, the MDRSA 01ST001 strain was treated with the 7,10-EODA (E 100 µg) of the present invention, streptomycin (S, 100 µg), ampicillin (A, 100 µg), oxacillin (O, 100 µg), vancomycin (V, 100 µg), or penicillin (P, 100 µg), according to the method described in Experimental Example 5.

In addition, in order to confirm the antimicrobial activity according to the concentration of 7,10-EODA of the present invention, the concentration of 7,10-EODA was treated with 50µ (E1), 100 µg (E2), 200 µg (E3), and 400 µg (E4), respectively, and further treated with oxacillin (O, 100 µg) or vancomycin (V, 100 µg).

In addition, in order to confirm the effect of the combination treatment of the beta-lactam antibiotic against the MDRSA strain 01ST001 and the 7,10-DMA of the present invention, the beta-lactam antibiotic oxacillin (5 µg) or ampicillin (5 µg)+7,10-DMA (31.2 µg) treatment group (A); oxacillin (100 µg) or ampicillin (100 µg)+7,10-EODA (31.2 µg) treatment group (B); oxacillin (5 µg) or ampicillin (5 µg) single group (a); oxacillin (100 µg) or ampicillin (100 µg) single group (b); and 7,10-EODA (31.2 µg) single group (S) were treated. The results are illustrated in FIG. 4 to FIG. 7.

Figure 4:
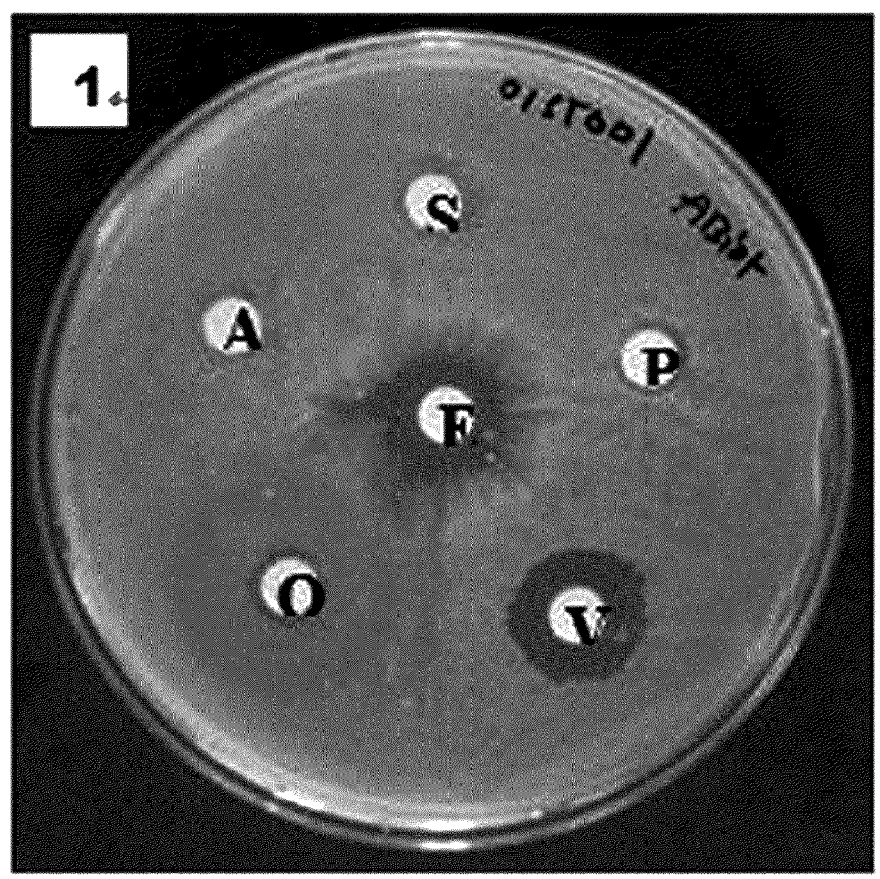
FIG. 4 is a diagram comparing the antimicrobial activity of 7,10-EODA or antibiotics of the present invention against MDRSA 01ST001 strain (illustrating the respective treatment of streptomycin 100 µg indicated by S, ampicillin 100 µg indicated by A, oxacillin 100 µg indicated by O, vancomycin 100 µg indicated by V, penicillin 100 µg indicated by P, and 7,10-EODA 100 µg indicated by E).

As illustrated in FIG. 4, the MDRSA 01ST001 strain was confirmed to be resistant to streptomycin (S), ampicillin (A), oxacillin (0), and penicillin (P). However, it was confirmed that the 7,10-EODA (E) of the present invention showed the antimicrobial activity against MDRSA 01ST001 strain.

Figure 5:
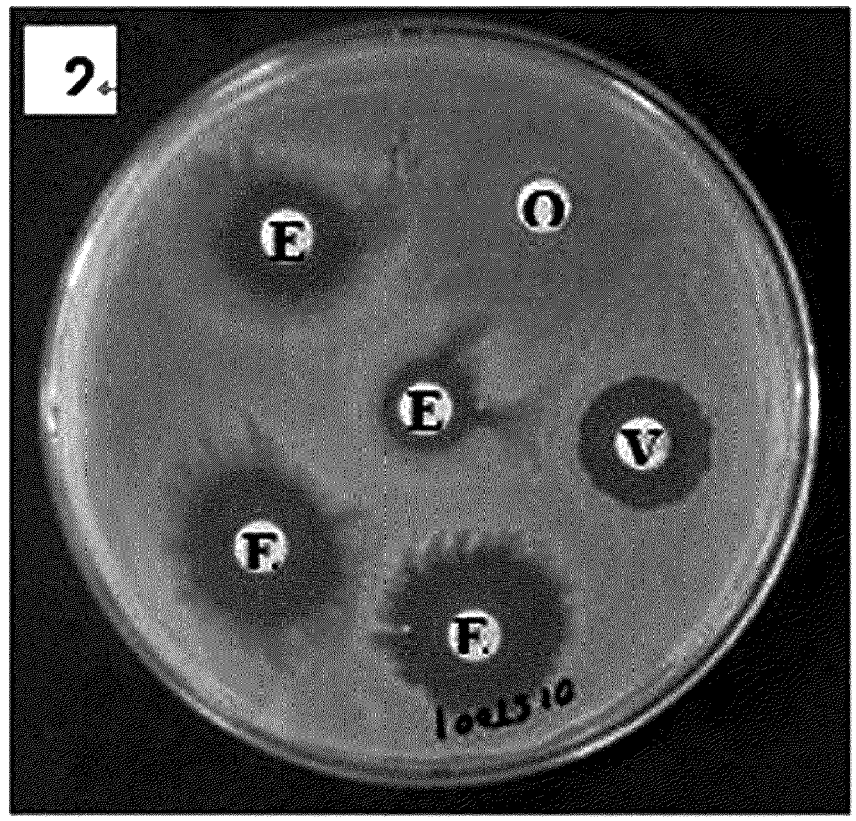
FIG. 5 is a diagram confirming the antimicrobial activity according to the concentration of 7,10-EODA of the present invention (illustrating the respective treatment of vancomycin 100 µg indicated by V, oxacillin 100 µg indicated by O, 7,10-EODA 50 µg indicated by E1, 7,10-EODA 100 µg indicated by E2, 7,10-EODA 200 µg indicated by E3, and 7,10-EODA 400 µg indicated by E4).

As illustrated in FIG. 5, it was confirmed that the antimicrobial activity against the MDRSA 01ST001 strain was high in a concentration-dependent manner of the 7,10-EODA of the present invention.

Figure 6:
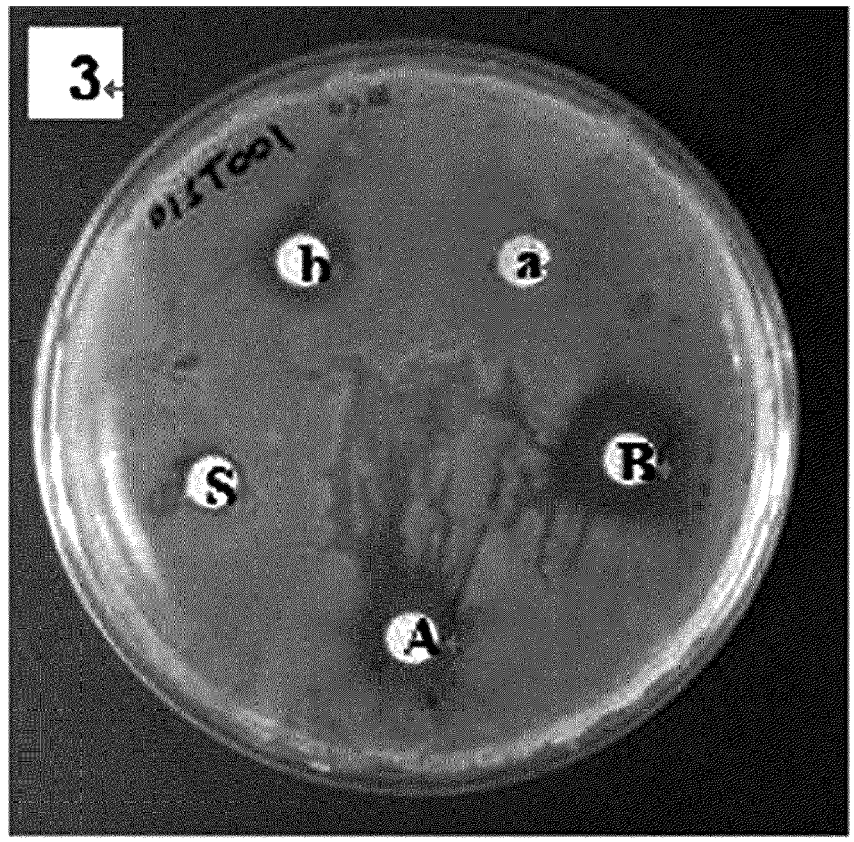
FIGS. 6 and 7 are diagrams comparing the antimicrobial activity after combination treatment with 7,10-EODA, oxacillin (FIG. 6) and ampicillin (FIG. 7) of the present invention (a refers to 5 µg of each antibiotic alone, b refers to 100 µg of each antibiotic alone, A refers to the co-treatment of 5 µg of each antibiotic and 31.2 µg of 7,10-EODA, B refers to the co-treatment of 100 µg of each antibiotic and 31.2 µg of 7,10-EODA, and S refers to 7,10-EODA 31.2 µg).

As illustrated in FIG. 6, when the oxacillin and the 7,10-EODA of the present invention were used as antibiotics, the antimicrobial activity against the MDRSA 01ST001 strain was significantly higher than the treatment of the oxacillin single group and 7,10-EODA single group.

Figure 7:
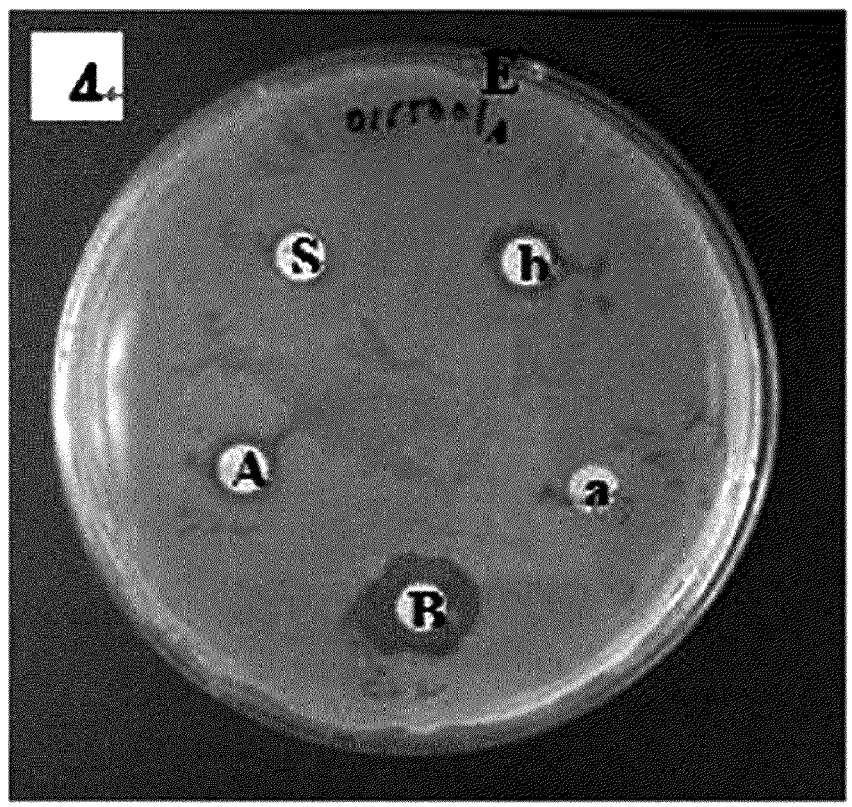

As illustrated in FIG. 7, when the ampicillin and the 7,10-EODA of the present invention were used as antibiotics, the antimicrobial activity against the MDRSA 01ST001 strain was significantly higher than the treatment of the ampicillin single group and 7,10-EODA single group.

Example 4

Confirmation of the Synergistic Effect of Antimicrobial Activity According to Combination Treatment of 7,10-EODA and Penicillin on MDRSA Strain The synergistic effect on the antimicrobial activity according to a combination treatment of 7,10-EODA and penicillin against multidrug-resistant *Staphylococcus aureus* (MDRSA) was confirmed.

Specifically, the method described in Experimental Example 4 was used, and the concentration of penicillin was gradually reduced by ½ at a maximum concentration from 0 to a maximum of 350 (µg/mL) for treatment. Herein, 7,10-EODA of the present invention was treated with 0, 7.5, and 15.0 µg/mL, respectively. Cell growth of the MDRSA 01ST001 strain was then measured at an optical density of 600 nm ($OD_{600}$). The results are illustrated in FIG. 8.

Figure 8:
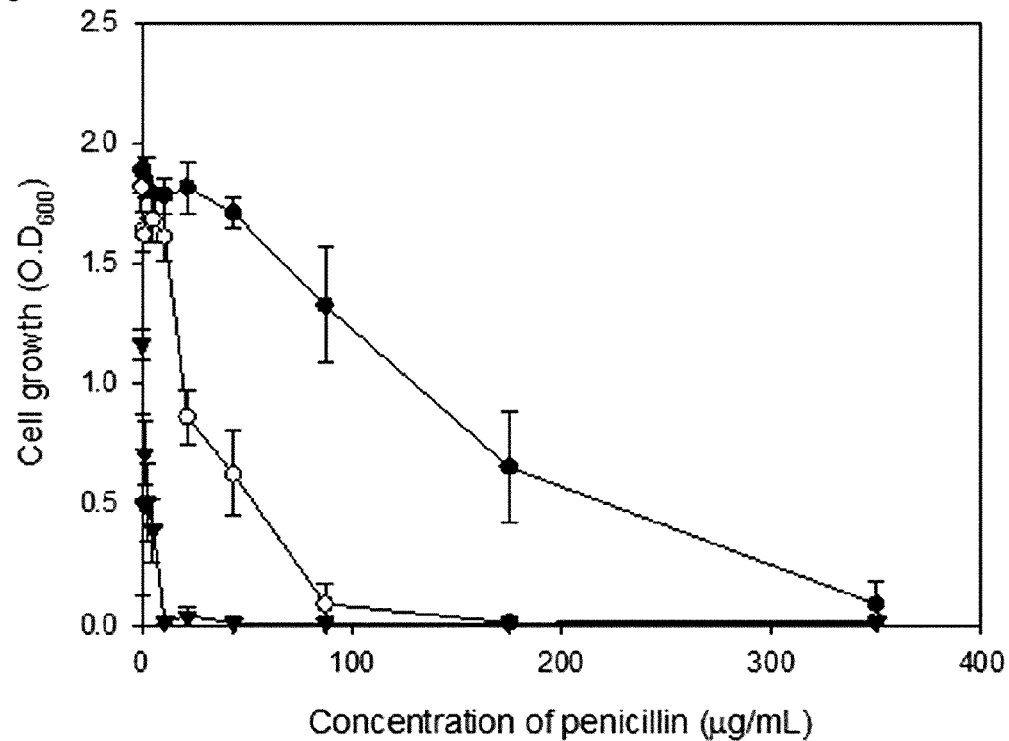
FIG. 8 is a graph illustrating the results of confirming the synergistic effect of the antimicrobial activity according to the treatment concentration in the combination treatment of penicillin against MDRSA 01ST001 strain and 7,10-EODA of the present invention (in which ● refers to the untreatment of 7,10-EODA, ○ refers to the concentration treatment of 7.5 µg/mL of 7,10-EODA, and ▼ refers to the concentration treatment of 15.0 µg/mL of 7,10-EODA).

As illustrated in FIG. 8, even when penicillin was treated at the same concentration, it was confirmed that when the concentration of 7,10-EODA to be used in combination increases, the growth of MDRSA 01ST001 strain is effectively inhibited. Specifically, when the $MIC_{90}$ value was determined to inhibit growth and development of 90% or higher of the initial cell concentration, it was confirmed that the $MIC_{90}$ value of penicillin was 350 µg/mL when 7,10-EODA was not used in combination. On the other hand, when treated in combination with a concentration of 7.5

μg/mL corresponding to 1/16 of the original $MIC_{90}$ value of 7,10-EODA, the $MIC_{90}$ value of penicillin was reduced to 87.5 μg/mL, and when treated in combination with a concentration of 15.0 μg/mL corresponding to 1/8 of the original $MIC_{90}$ value of 7,10-EODA, the $MIC_{90}$ value of penicillin was significantly reduced to 10.9 μg/mL.

Therefore, when the 7,10-EODA of the present invention was originally treated at a concentration of 1/8 or 1/16 of the original $MIC_{90}$ value, the degree of decrease of the $MIC_{90}$ value of the penicillin treated with the 7,10-EODA of the present invention was reduced to 1/4 and 1/32, respectively, as compared to the case that 7,10-EODA was not treated in combination. Therefore, it was confirmed that the antimicrobial activity synergistic effect was exhibited by the combination treatment of 7,10-EODA of the present invention.

Example 5

Confirmation of the Antimicrobial Activity Synergistic Effects According to the Combination Treatment of 7,10-EODA and Each Antibiotic on Multidrug-Resistant *Staphylococcus aureus* (MDRSA)

For the multidrug-resistant *Staphylococcus aureus* (MDRSA) strain (MDRSA 01ST001) or the non-drug-resistant *Staphylococcus aureus* (ATCC 29213) strain, the antimicrobial activity synergistic effect for the combination treatment of each antibiotic on the treatment of 7,10-EODA was confirmed.

Specifically, the minimal inhibitory concentration (MIC) was measured according to the method of Experimental Example 4 above, and the degree of inhibition (Agar diffusion analysis) (zone of inhibition; ZOI) was measured according to the method of Experimental Example 5 above. Antibiotics include streptomycin (STP), ciprofloxacin (CIP), chloramphenicol (CPL), chlorpromazine (CPZ), rifampicin (RIF), irgasan (IRG), trimethoprim (TMP), oxacillin (OXA), ampicillin (AMP), cephalexin (CEP), or penicillin (PEN), of which they were used at a concentration of 1/2×MIC, respectively. 7,10-EODA (1/4×MIC) of the present invention was treated or non-treated with the antibiotics to confirm the combination treatment synergistic effect for the multidrug-resistant *Staphylococcus aureus* (MDRSA) strain (MDRSA 01ST001) or the non-drug-resistant *Staphylococcus aureus* (ATCC 29213) strain. The results are shown in Table 1 below.

TABLE 1

| Antibiotic | MIC (μg/ml) | | ZOI (mm) without/with 7.10-EODA | |
|---|---|---|---|---|
| | 001 | 29213 | 001 | 29213 |
| STP | 62.5 | 3.0 | 6.0 ± 0.0/12.9 ± 0.2 | 6.0 ± 0.0/11.4 ± 0.7 |
| CIP | 6.0 | 2.5 | 6.0 ± 0.0/13.2 ± 0.1 | 9.6 ± 0.2/13.2 ± 0.2 |
| CPL | 10.0 | 10.0 | 13.2 ± 0.4/13.9 ± 0.4 | 7.4 ± 0.2/7.21 ± 0.2 |
| CPZ | 62.5 | 125.0 | 7.2 ± 0.1/12.0 ± 0.5 | 6.0 ± 0.0/8.05 ± 0.5 |
| RIF | 5.0 | 5.0 | 18.3 ± 0.2/20.2 ± 0.1 | 21.0 ± 0.8/23.7 ± 1.2 |
| IRG | 0.1 | 0.1 | 12.4 ± 0.3/13.8 ± 1.1 | 11.1 ± 0.5/10.0 ± 0.3 |
| TMP | 7.8 | 7.8 | 6.0 ± 0.0/6.00 ± 0.0 | 8.9 ± 0.1/12.3 ± 0.2 |
| OXA | 62.5 | 0.04 | 6.0 ± 0.1/14.1 ± 0.2 | 8.3 ± 0.1/9.60 ± 0.4 |

TABLE 1-continued

| Antibiotic | MIC (μg/ml) | | ZOI (mm) without/with 7.10-EODA | |
|---|---|---|---|---|
| | 001 | 29213 | 001 | 29213 |
| AMP | 1000.0 | 1.97 | 7.3 ± 0.2/14.2 ± 0.6 | 16.9 ± 0.3/17.0 ± 0.5 |
| CEP | 1000.0 | 1.97 | 10.1 ± 1.3/13.1 ± 0.6 | 15.3 ± 0.1/15.3 ± 0.2 |
| PEN | 1000.0 | 0.5 | 7.1 ± 0.1/13.6 ± 0.5 | 12.9 ± 0.4/13.2 ± 0.4 |

As shown in Table 1, when the 7,10-EODA of the present invention was treated in combination not only with oxacillin, ampicillin, and penicillin, which are beta-lactam antibiotics, but also with streptomycin and ciprofloxacin, it was confirmed that strong antimicrobial activity effect was exhibited in the multidrug-resistant *Staphylococcus aureus* strain (MDRSA 01ST001). In addition, when the antibiotic and the 7,10-EODA of the present invention were treated in combination, it was confirmed that the ZOI (mm) value was increased to about 92-135% as compared with the antibiotic single treatment group, and in combination treatment, it was confirmed that the antimicrobial activity effect was significantly increased.

Example 6

Confirmation of the Antimicrobial Activity Synergistic Effects According to the Combination Treatment of 7,10-EODA and Each Antibiotic on Multidrug-Resistant *Staphylococcus aureus* (MDRSA) and *Staphylococcus aureus* Strains The antimicrobial activity synergistic effects according to the combination treatment of 7,10-EODA and each antibiotic on methicillin-resistant *Staphylococcus aureus* (MRSA) strains 085, 093, 120, 136, and 165, MDRSA 01ST001, which is a multidrug-resistant *Staphylococcus aureus* (MDRSA) strain, *E. coli* ATCC 8739, and *S. typhimurium* KCTC 2515 were confirmed. According to the method described in Experimental Example 6 above, an oxacillin single group (O), an ampicillin single group (A), a 7,10-EODA single group (E), a combination treatment group of oxacillin and 7,10-EODA (O+E), and a combination treatment group of ampicillin and 7,10-EODA (A+E) were placed, and 7,10-EODA was treated at a concentration of 31.2 μg/mL (1/4×MIC). Fractional inhibitory concentration indices (FICI) values accordingly were confirmed. The results are shown in Table 2 below.

TABLE 2

| STRAIN | MIC (μg/ml) | | | MIC in combination (μg/ml) | | FICI | |
|---|---|---|---|---|---|---|---|
| | O | A | E | O + E | A + E | O + E | A + E |
| 085 | 250.0 | 1000.0 | 125.0 | 7.81 | 62.5 | 0.15 | 0.31 |
| 093 | 2000.0 | 31.2 | 125.0 | 125 | 3.90 | 0.31 | 0.37 |
| 165 | 31.2 | 2000.0 | 125.0 | 3.90 | 7.81 | 0.37 | 0.25 |
| 120 | 250.0 | 250.0 | 125.0 | 31.2 | 7.81 | 0.37 | 0.28 |
| 136 | 62.5 | 1000.0 | 125.0 | 3.90 | 15.6 | 0.31 | 0.26 |
| 001 | 62.5 | 1000.0 | 125.0 | 3.90 | 62.5 | 0.37 | 0.31 |
| 8739 | 200.0 | 0.6 | 500.0 | 200 | 0.6 | 2 | 2 |
| 2515 | 250.0 | 0.6 | 500.0 | 250 | 0.6 | 2 | 2 |

As shown in Table 2, as for MRSA and MDRSA strains, when the 7,10-EODA of the present invention was treated in combination with oxacillin, the FICI value was in the range of 0.25 to 0.37 and 0.299 on the average, confirming the antimicrobial activity synergistic effect, whereas *E. coli* ATCC 8739 and *S. typhimurium* KCTC 2515, which are gram-negative bacteria, showed an FICI value of 2.0, confirming the antimicrobial activity.

Example 7

Confirmation of Incubation Time and Growth of MDRSA 01ST001 Strain by 7,10-DMA and Antibiotic Combination Treatment Each incubation time condition; and the growth of MDRSA 01ST001 strain according to the combination treatment conditions of 7,10-EODA and antibiotics were confirmed.

Specifically, in accordance with the method of Experimental Example 7 above, (a) 7,10-EODA treatment group of 15.6 μg concentration (⅛×MIC), (b) 7,10-EODA treatment group of 31.2 μg concentration (¼×MIC), (c) oxacillin of 3.9 μg concentration, and 7,10-EODA of 15.6 μg concentration+oxacillin treatment group (a+c) of 3.9 μg concentration, and 7,10-EODA treatment group of 31.2 μg concentration+oxacillin treatment group (b+c) of 3.9 μg concentration were placed. In addition, the growth of MDRSA 01ST001 strain was confirmed by cell density under the conditions of incubation time of 5, 10, 15, 20, 25, and 30 hours. The results are illustrated in FIG. 9.

Figure 9:
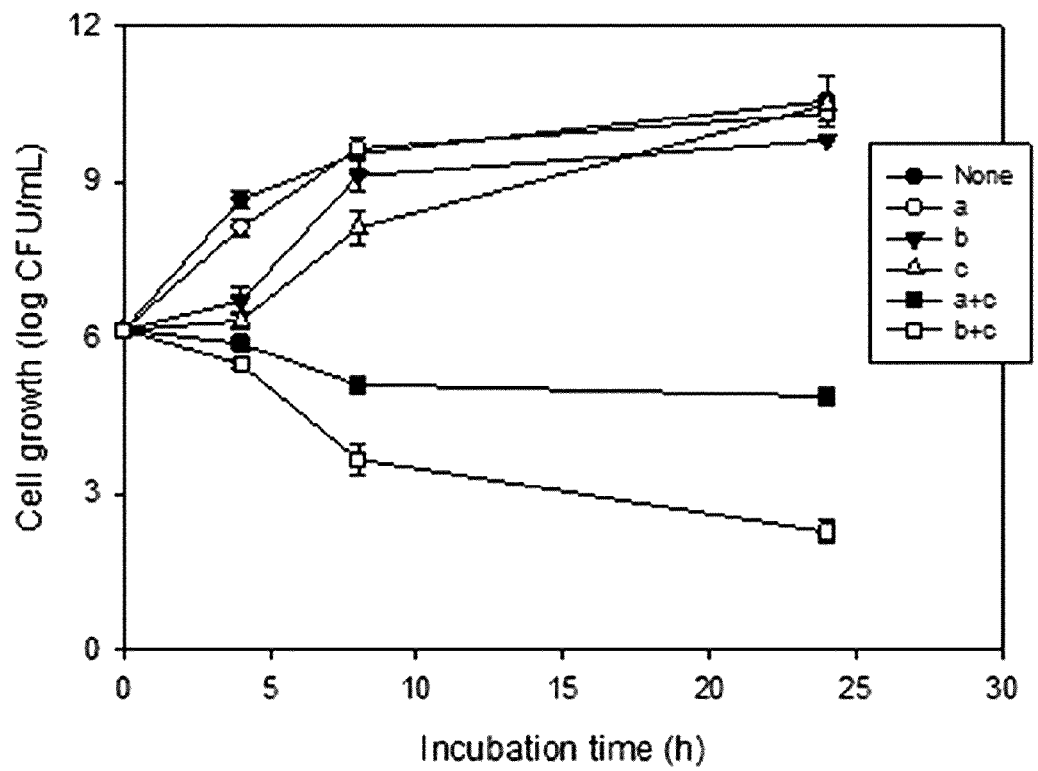
FIG. 9 is a graph illustrating the results of confirming the incubation time and the growth and development of MDRSA 01ST001 strain according to the combination treatment with 7,10-EODA and antibiotics.

As illustrated in FIG. 9, the cell density of the MDRSA 01ST001 strain rapidly increased to 8.7 log CFU/mL in the control group treated with nothing. In addition, it was confirmed that the cell density was reduced to 1.30 log CFU/mL in the oxacillin treatment group (a+c) of 7,10-EODA+3.9 μg concentration of 15.6 μg concentration under the condition of culture for 24 hours compared to the control group. In addition, the cell density was rapidly decreased to 2.5 log CFU/mL in the 7,10-EODA treatment group of 31.2 μg concentration+oxacillin treatment group of 3.9 μg concentration (b+c) under the condition of culture for 8 hours, and cell density of 3.9 log CFU/mL was observed under the condition of culture for 24 hours. Thus, it was confirmed that the combination treatment of 7,10-EODA and oxacillin as an antibiotic, of the present invention effectively inhibited the growth of MDRSA 01ST001 strain having multidrug resistance over time.

Example 8

Confirmation of Synergistic Effect of Antimicrobial Activity Against MRSA, MDRSA, or MSSA Strains by Combination Treatment of 7,10-EODA and Non-Beta-Lactam (Non-β-Lactam) Antibiotics The synergistic effect of antimicrobial activity against MRSA, MDRSA, or MSSA strains by combination treatment of 7,10-EODA and non-beta-lactam (non-β-Lactam) Antibiotics was Confirmed.

Figure 10:
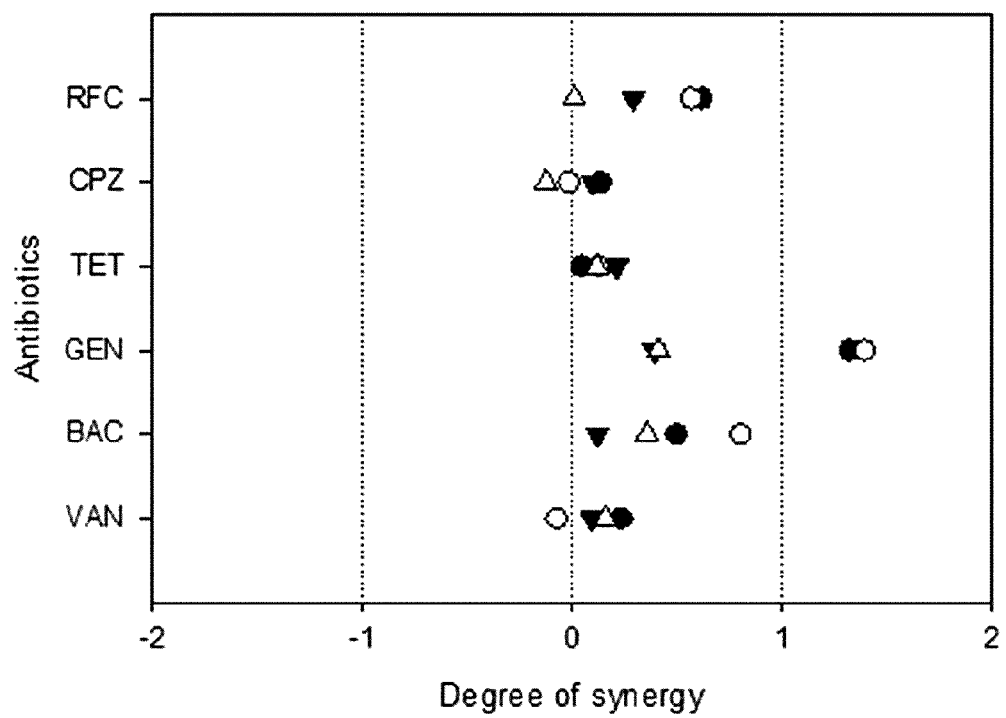
FIG. 10 is a graph illustrating the results of confirming the synergistic effect of the antimicrobial activity against MRSA or MSSA strains in the combination treatment with 7,10-EODA and non-β-lactam antibiotics (in which ● refers to MRSA 01ST 018, ○ refers to MDRSA 01ST 001, Δ refers to *S. aureus* ATCC 29213, and ▼ refers to *S. aureus* 1199).

The results are illustrated in FIG. 10. Specifically, in accordance with the method described in Experimental Example 6, ATCC 29213 (black inverted triangle), which is MSSA (methicillin-sensitive *Staphylococcus aureus*) strain, MDRSA (multidrug-resistant *Staphylococcus aureus*) 01ST001 strain (white circle), MRSA (methicillin-resistant *Staphylococcus aureus*) 01ST018 (black circle), and clinical isolate *S. aureus* 1199 strain (white triangle) were used. Each of the strains was cultured after combination treatment of 7,10-EODA and antibiotics (¼×MIC) at a concentration of 15.6 μg/mL (⅛×MIC) for 24 hours. The antibiotics include rifampicin (RFC), chlorpromazine (CPZ), tetracycline (TET), gentamicin (GEN), bacitracin (BAC), and vancomycin (VAN), respectively.

As illustrated in FIG. 10, when the 7,10-EODA of the present invention was used in combination with gentamicin, it was confirmed that a high synergy index of 1.32 or 1.37 was obtained for the MRSA 018 strain or the MDRSA 01ST001 strain, respectively. In addition, when the combination of the 7,10-EODA of the present invention and bacitracin or rifampicin were treated on the MDRSA 01ST001 strain, it was confirmed that the synergy index was 0.8 and 0.6, respectively.

Accordingly, through the above class of results, when the 7,10-EODA of the present invention was used in combination with various antibiotics, it was confirmed that the antimicrobial activity synergistic effect against *Staphylococcus aureus* of various intrinsic properties was shown without antagonism. In addition, it was confirmed that the 7,10-EODA of the present invention is excellent in antimicrobial activity and antibacterial activity synergistic effect in combination with various antibiotics besides beta-lactam antibiotics.

Example 9

Microbial Growth Inhibitory Effect of 7,10-epoxyoctadeca-7,9-dienoic acid (7,10-EODA)

In order to confirm the microbial growth inhibitory effect of 7,10-epoxyoctadeca-7,9-dienoic acid (7,10-EODA), 1 ml of YDP medium was dispensed into a 24-well dish, and then 7,10-epoxyoctadeca-7,9-dienoic acid (7,10-EODA) diluted with DMSO was added to each well at various concentrations ranging from 0 to 250 μg/ml.

Figure 11:
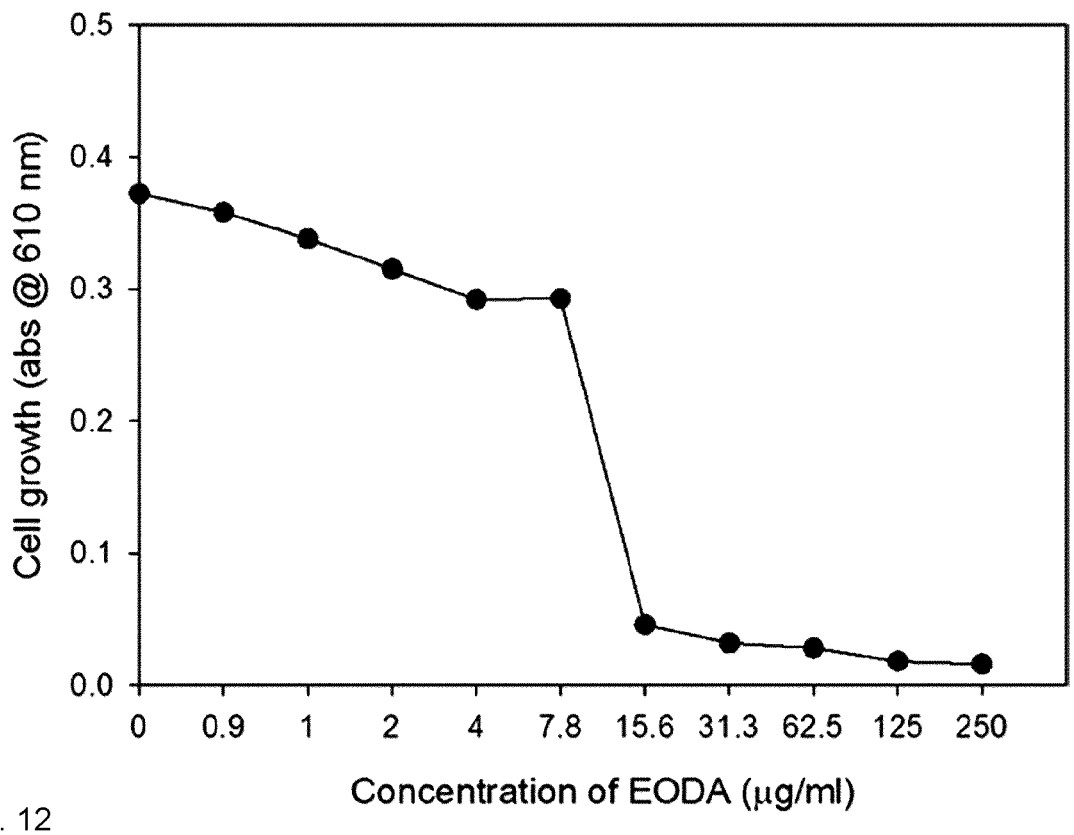
FIG. 11 is a graph illustrating the growth inhibition effect of a microorganism (MDRSA 01ST001) according to the treatment concentration of 7,10-epoxyoctadeca-7,9-dienoic acid (7,10-EODA) according to one embodiment of the present invention.

Methicillin-resistant *Staphylococcus aureus* (MRSA) 01ST001 was inoculated in 100 μl of each well to which 7,10-epoxyoctadeca-7,9-dienoic acid (7,10-EODA) was added and cultured for 12 hours. After 12 hours of culture, the culture medium was recovered from each well, and the medium component was removed by centrifugation. After washing twice with distilled water, the absorbance was measured at 610 nm to measure the degree of microbial growth. The amount of measured microorganisms was plotted on a graph to determine the concentration of 7,10-EODA in which the microorganisms did not grow as the minimum limiting concentration. The results are illustrated in FIG. 11. At this time, 7,10-EODA was not added as a control.

As illustrated in FIG. 11, as the concentration of 7,10-epoxyoctadeca-7,9-dienoic acid (7,10-EODA) was increased, the concentration of residual viable microorganisms gradually decreased. In the treatment concentration of 15.6 μg/ml, it showed more than 90% reduction compared to the control. From these results, it was found that the $MIC_{90}$ concentration of 7,10-epoxyoctadeca-7,9-dienoic acid (7,10-EODA) as an active ingredient of the present invention to MDRSA 01ST001 was 15.6 ppm or less.

Example 10

Microbial Growth Inhibitory Effect of 7,10-epoxyoctadeca-7,9-dienoic acid (7,10-EODA) Over Incubation Time In order to confirm the microbial growth inhibitory effect over incubation time after the treatment of 7,10-epoxyoctadeca-7,9-dienoic acid (7,10-EODA), in Example 9 above, 7,10-epoxyoctadeca-7,9-dienoic acid (7,10-EODA) was added at concentrations of 0, 15.6, 31.3, 62.5, and 125 μg/ml, and the degree of microbial growth was measured. The results are illustrated in FIG. 12.

Figure 12:
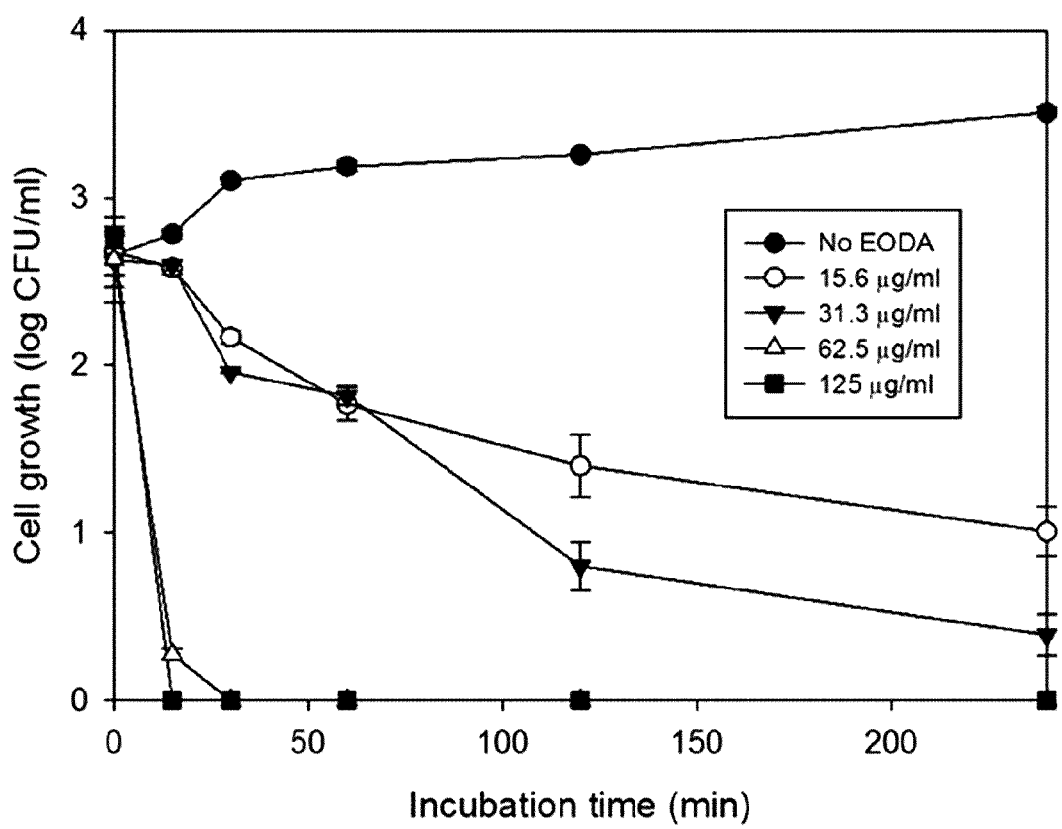
FIG. 12 is a graph illustrating the concentration of the residual viable microorganisms (MDRSA 01ST001) by time according to the treatment concentration of 7,10-epoxyoctadeca-7,9-dienoic acid (7,10-EODA) according to one embodiment of the present invention.

As illustrated in FIG. 12, at 15.6 μg/ml of 7,10-epoxyoctadeca-7,9-dienoic acid (7,10-EODA), the residual viable microorganism concentration after 4 hours of culture decreased by 50% or more as compared to the control.

And the residual viable microorganism concentration decreased to less than 10% after 10 minutes of culture at 62.5 μg/ml as compared to the control. In addition, at the treatment concentration of 125 μg/ml, it was confirmed that MDRSA 01ST001 was completely killed within 10 minutes after the start of the culture.

Example 11

Figure 13:
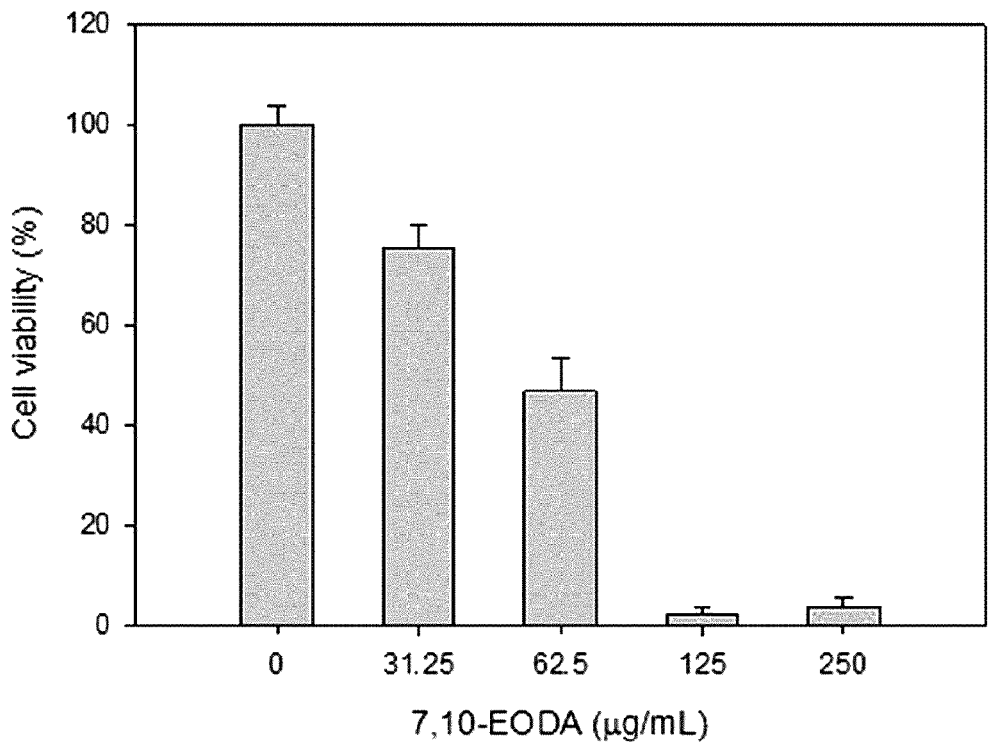
FIG. 13 illustrates the results of measuring the cytotoxicity of 7,10-EODA of the present invention.
Figure 14:
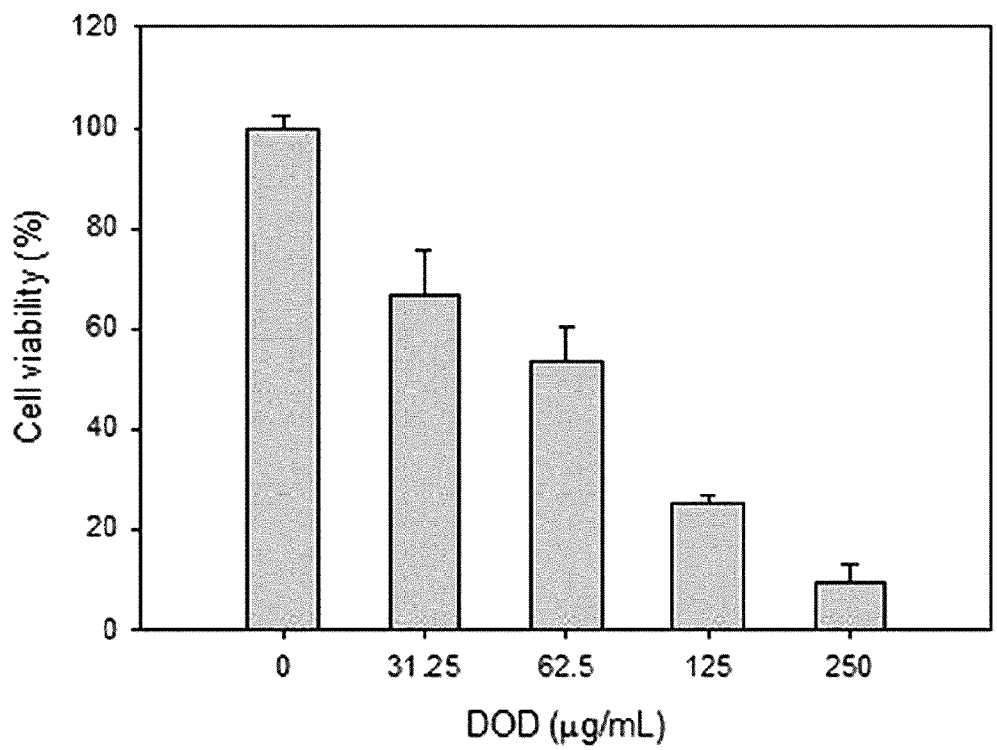
FIG. 14 illustrates the results of measuring the cytotoxicity of DOD.
Figure 15:
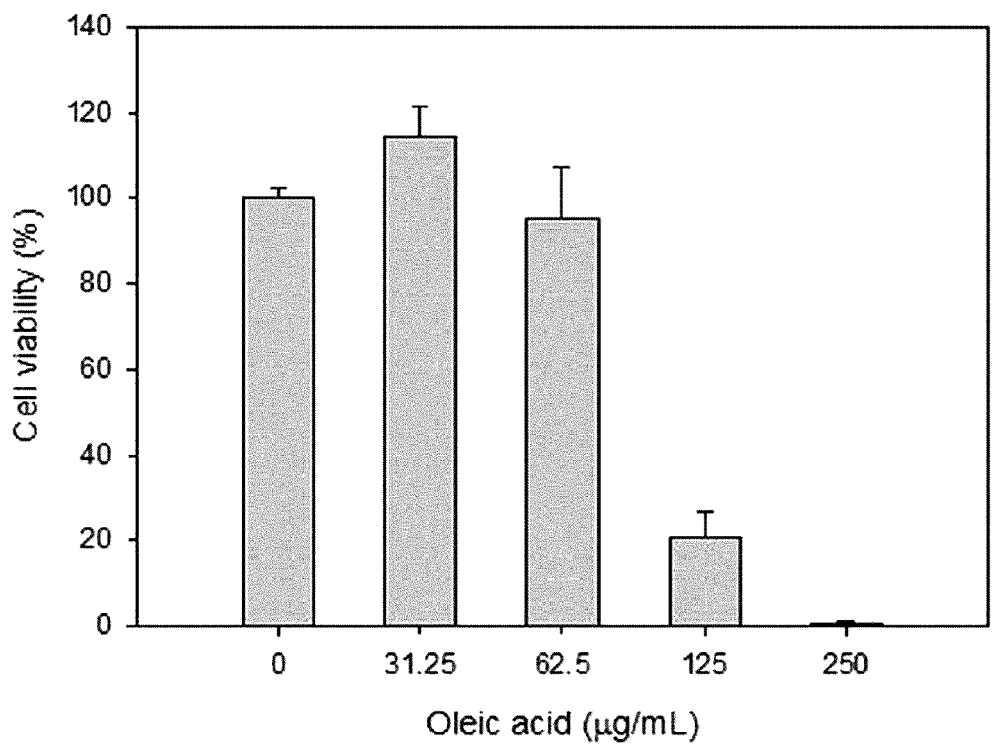
FIG. 15 illustrates the results of measuring the cytotoxicity of oleic acids.
Figure 16:
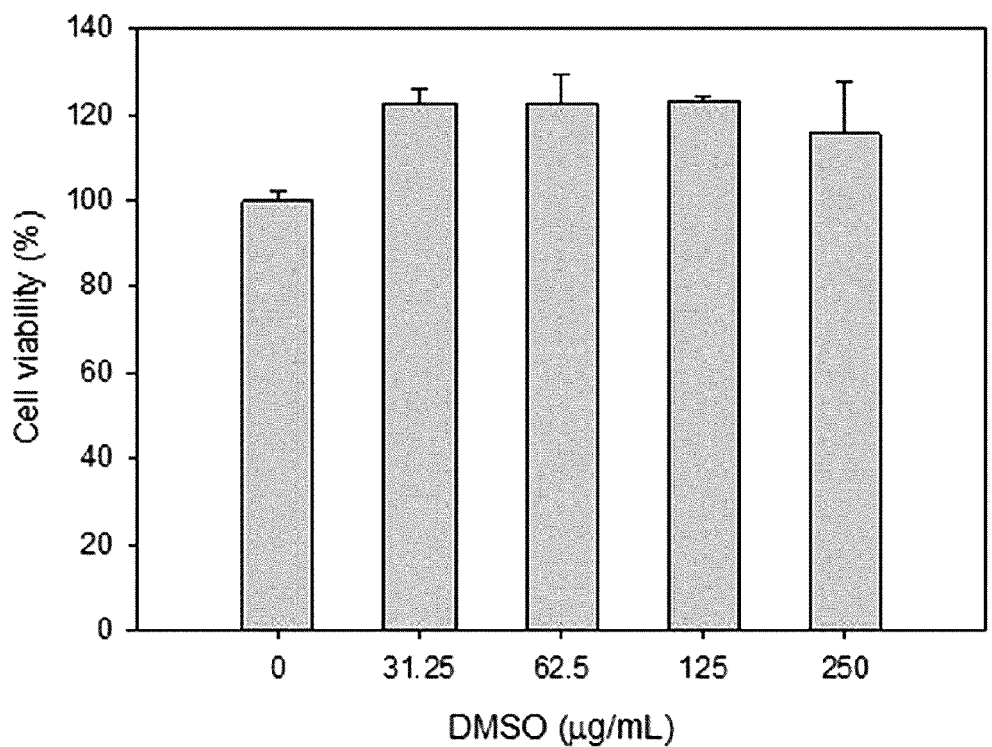
FIG. 16 illustrates the results of measuring the cytotoxicity of DMSO.
Figure 17:
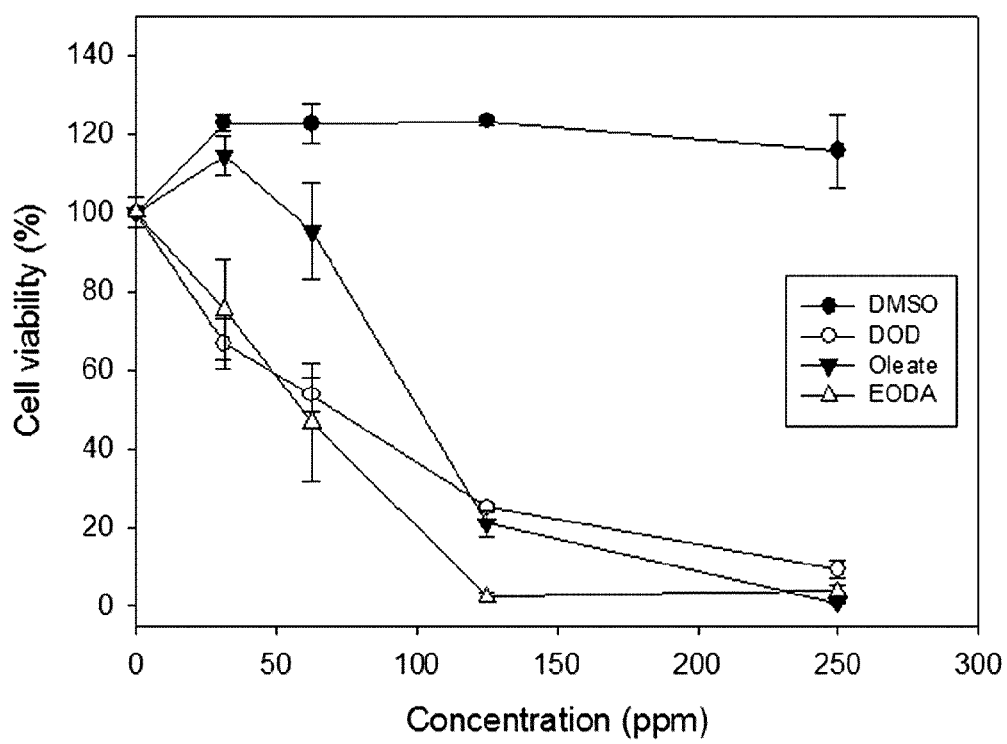
FIG. 17 is a graph illustrating the cell survival rate according to the concentration of 7,10-EODA, DOD, oleic acids, and DMSO of the present invention together.

Toxicity Test of 7,10-epoxyoctadeca-7,9-dienoic acid (7,10-EODA), DOD, Oleic Acid, and DMSO Simple toxicity tests were performed for the four components of 7,10-EODA, DOD, oleic acid, and DMSO. The target cells were HepG2 animal cells and the results were obtained by MTT assay. In the case of 7,10-EODA, it is illustrated in FIG. 13, in the case of DOD, it is illustrated in FIG. 14, in the case of oleic acids, it is illustrated in FIG. 15, and in case of DMSO, it is illustrated in FIG. 16. The cell viability according to the concentration of the four components is also illustrated in FIG. 17. In the case of 7,10-EODA, the value of $LD_{50}$ was about 62.5, which is similar to that of DOD, which is a component for synthesizing 7,10-EODA. In comparison with about 100, which is $LD_{50}$ values of fatty acid oleic acid used as a substrate for DOD production, it was slightly lower than that thereof, but it was confirmed that 7,10-EODA as a whole was not highly toxic. In this regard, it was confirmed that 7,10-EODA had toxicity enough to be used in the human body.

Through the results as above, it could be expected that the 7,10-epoxyoctadeca-7,9-dienoic acid (7,10-EODA), an active ingredient of the present invention, exhibited excellent antimicrobial activity against multidrug-resistant *Staphylococcus aureus* and microbial growth inhibitory effect, and thus can be used very usefully as multidrug-resistant *Staphylococcus aureus* antimicrobial agents. In addition, the 7,10-epoxyoctadeca-7,9-dienoic acid (7,10-EODA) of the present invention exhibits a strong antibacterial activity against multidrug-resistant *Staphylococcus aureus*, and thus is very effective in prevention, improvement, or treatment of infectious diseases caused by microorganisms.

Preparation Example 1. Preparation of Pharmaceutical Formulations

Powder Preparation 20 mg of 7,10-epoxyoctadeca-7,9-dienoic acid (7,10-EODA) of Experimental Example 1, 100 mg of lactose, and 10 mg of talc were mixed and filled in an airtight container, and a powder preparation was prepared by a conventional method.

Tablet Preparation 10 mg of 7,10-epoxyoctadeca-7,9-dienoic acid (7,10-EODA) of Example 1, 100 mg of corn starch, 100 mg of lactose and 2 mg of magnesium stearate were mixed, and compressed to create a uniform shape to prepare each tablet.

Capsule Preparation 10 mg of 7,10-epoxyoctadeca-7,9-dienoic acid (7,10-EODA) of Experimental Example 1, 3 mg of crystalline cellulose, 14.8 mg of lactose, and 0.2 mg of magnesium stearate were mixed and filled in a gelatin capsule by a conventional method to prepare each capsule.

Injection Preparation 10 mg of 7,10-epoxyoctadeca-7,9-dienoic acid (7,10-EODA) of Experimental Example 1 per ampoule (2 mL), 180 mg of mannitol, 2,974 mg of sterile distilled water for injection, and 26 mg of Na2HPO4 2H2O were used to prepare each injection by a conventional method.

Liquid Preparation 20 mg of 7,10-epoxyoctadeca-7,9-dienoic acid (7,10-EODA) of Experimental Example 1, 10 g of isomerized glucose syrup, and 5 g of mannitol were added to purified water and dissolved, and a lemon flavor was added in an appropriate amount, and then the above ingredients were mixed. Then, purified water was further added thereto, adjusted to a total volume of 100 mL, filled in a brown bottle, sterilized, and each liquid preparation was prepared by a conventional method.

Preparation Example 2. Preparation of Cosmetic Preparations

Softening Face Lotion Preparation 0.1% by weight of 7,10-epoxyoctadeca-7,9-dienoic acid (7,10-EODA) of Experimental Example 1, 5.2% by weight of 1,3-butylene glycol, 1.5% by weight of oleyl alcohol, 3.2% by weight of ethanol, 3.2% by weight of polysorbate 20, 2.0% by weight of benzophenone-9, 1.0% by weight of carboxyl vinyl polymer, 3.5% by weight of glycerin, a small amount of fragrance, a small amount of preservative, and a remaining amount of purified water were mixed to prepare each Softening face lotion.

Milk Lotion Preparation 0.1% by weight of 7,10-epoxyoctadeca-7,9-dienoic acid (7,10-EODA) of Experimental Example 1, 5.1% by weight of glycerin, 4.2% by weight of propylene glycol, 3.0% by weight of tocopheryl acetate, 4.6% by weight of liquid paraffin, 1.0% by weight of triethanolamine, 3.1% by weight of squalane, 2.5% by weight of macadamia nut oil, 1.6% by weight of polysorbate 60, 1.6% by weight of sorbitan sesquirolate, 0.6% by weight of propylparaben, 1.5% by weight of carboxyl vinyl polymer, trace amount of fragrance, trace amount of preservative, and remaining amount of purified water were mixed to prepare each milk lotion by a conventional method.

Nutrition Cream Preparation 0.5% by weight of 7,10-epoxyoctadeca-7,9-dienoic acid (7,10-EODA) of Experimental Example 1, 4.0% by weight of glycerin, 3.5% by weight of Vaseline, 2.1% by weight of triethanolamine, 5.3% by weight of liquid paraffin, 3.0% by weight of squalene, 2.6% by weight of beeswax, 5.4% by weight of tocopheryl acetate, 3.2% by weight of polysorbate 60, 1.0% by weight of carboxyl vinyl polymer, 3.1% by weight of sorbitan sesquioleate, trace amount of fragrance, trace amount of preservative, and remaining amount of purified water were mixed to prepare each nutrition cream by a conventional method.

Massage Cream Preparation 0.5% by weight of 7,10-epoxyoctadeca-7,9-dienoic acid (7,10-EODA) of Experimental Example 1, 4.0% by weight of glycerin, 3.5% by weight of Vaseline, 0.5% by weight of triethanolamine, 24.0% by weight of liquid paraffin, 3.0% by weight of squalane, 2.1% by weight of beeswax, 0.1% by weight of tocopheryl acetate, 2.4% by weight of polysorbate 60, 1.0% by weight of carboxyl vinyl polymer, 2.3% by weight of sorbitan sesquioleate, trace amount of fragrance, trace amount of preservative, and remaining amount of purified water were mixed to prepare each massage cream by a conventional method.

Preparation Example 3. Preparation of Food Preparations

Health Food Manufacturing 100 mg of 7,10-epoxyoctadeca-7,9-dienoic acid (7,10-EODA) of Experimental Example 1, a proper amount of vitamin mixture, 70 g of vitamin A acetate, 1.0 mg of vitamin E, 0.13 mg of vitamin B1, 0.15 mg of vitamin B2, 0.5 mg of vitamin B6, 0.2 g of vitamin B12, 10 mg of vitamin C, 10 g of biotin, 1.7 mg of nicotinamide, 50 g of folic acid, 0.5 mg of calcium pantothenate, a proper amount of mineral mixture, 1.75 mg of ferrous sulfate, 0.82 mg of zinc oxide, 25.3 mg of magnesium carbonate, 15 mg of potassium phosphate monobasic, 55 mg of calcium phosphate dibasic, 90 mg of potassium citrate, 100 mg of calcium carbonate, and 24.8 mg of magnesium chloride were mixed. Then granules were prepared and each health food was prepared by a conventional method. At this time, although the composition ratio of the vitamin and mineral mixture is mixed with ingredients relatively suitable for a health food as a preferred embodiment, the compounding ratio may be arbitrarily modified.

Health Drink Preparation 100 mg of 7,10-epoxyoctadeca-7,9-dienoic acid (7,10-EODA) of Experimental Example 1, 15 g of vitamin C, 100 g of vitamin E (powder), 19.75 g of ferrous lactate, 3.5 g of zinc oxide, 3.5 g of nicotine acid amide, 0.2 g of vitamin A, 0.25 g of vitamin B1, 0.3 g of vitamin B2, and a proper amount of water were mixed. After stirring and heating for about 1 hour at 85° C., the solution was filtered and filled in a sterilized 2 L container, sealed, sterilized, and stored in a refrigerator to prepare each health drink. At this time, although the composition ratio is mixed with the ingredients relatively suitable for the favorite drink as a preferred embodiment, it is also possible to arbitrarily modify the blending ratio according to the regional or national preference such as the demand class, demand country, and purpose of uses.

Preparation Example 4. Animal Feed Preparation

Feed Additive Preparation 100 g of 7,10-epoxyoctadeca-7,9-dienoic acid (7,10-EODA) of Experimental Example 1 and an appropriate amount of excipients were mixed to prepare feed additives according to the conventional method for preparing feed additives.

Feed Preparation 50 g of 7,10-epoxyoctadeca-7,9-dienoic acid (7,10-EODA) of Experimental Example 1, 200 g of mushroom medium, 30 g of wheat brp, 50 g of beet pulp, 220 g of rice distillers dried grains, 200 g of corn flakes, 40 g of full-fat soybean, 100 g of pulp, 200 g of corn silage, 180 g of maize cob, 400 g of bean-curd dregs, 323 g of rice glass, 14 g of zeolite, and 40 g of tapioca were mixed to prepare feed according to a conventional feed preparation method.

Although the present invention has been described by way of the preferred embodiments mentioned above, it is possible to make various modifications and variations without departing from the spirit and scope of the invention. It is also to be understood that the appended claims are intended to cover such modifications and variations falling within the scope of the invention.

The invention claimed is:

1. A method for treating a bacterial infectious disease comprising administering to a subject in need thereof an effective amount therefor of an antimicrobial composition comprising (A) 7,10-epoxyoctadeca-7,9-dienoic acid alone, or (B) a combination of 7,10-epoxyoctadeca-7,9-dienoic acid and an antibiotic wherein the bacterial infectious disease is food poisoning, wherein the antimicrobial composition exhibits an antimicrobial activity against at least one bacterium selected from the group consisting of *Staphylococcus aureus, Escherichia coli* and *Salmonella typhimurium*, and wherein the antibiotic is selected from the group consisting of penicillin class antibiotics, aminoglycoside class antibiotics, rifampicin class antibiotics, polypeptide class antibiotics and fluoroquinolone class antibiotics.

2. The method according to claim 1, when the antimicrobial composition comprises 7,10-epoxyoctadeca-7,9-dienoic acid alone, the content of 7,10-epoxyoctadeca-7,9-dienoic acid in the composition being a concentration of 0.01 to 3,000 µg/ml.

3. The method according to claim 1, wherein the antimicrobial composition comprises 7,10-epoxyoctadeca-7,9-dienoic acid and an antibiotic, and the content of the 7,10-epoxyoctadeca-7,9-dienoic acid is 0.01 to 5,000 µg/ml.

4. The method according to claim 1, wherein the antimicrobial composition exhibits an antimicrobial activity against an antibiotic resistant bacterium.

5. The method according to claim 1, wherein *Staphylococcus aureus* is at least one selected from the group consisting of multidrug-resistant *Staphylococcus aureus* (MDRSA), methicillin-resistant *Staphylococcus aureus* (MRSA), vancomycin resistant *Staphylococcus aureus* (VRSA), and vancomycin intermediate *Staphylococcus aureus* (VISA).

* * * * *